(12) United States Patent
Kallus et al.

(10) Patent No.: US 8,044,208 B2
(45) Date of Patent: Oct. 25, 2011

(54) IMIDAZOLE DERIVATIVES AS INHIBITORS OF TAFIA

(75) Inventors: Christopher Kallus, Frankfurt am Main (DE); Holger Heitsch, Frankfurt am Main (DE); Volkmar Wehner, Frankfurt am Main (DE)

(73) Assignee: Sanofi-Aventis, Paris (FR)

( * ) Notice: Subject to any disclaimer, the term of this patent is extended or adjusted under 35 U.S.C. 154(b) by 668 days.

(21) Appl. No.: 12/102,105

(22) Filed: Apr. 14, 2008

(65) Prior Publication Data
US 2008/0262028 A1    Oct. 23, 2008

Related U.S. Application Data

(63) Continuation of application No. PCT/EP2006/009500, filed on Sep. 30, 2006.

(30) Foreign Application Priority Data

Oct. 15, 2005 (DE) .......................... 10 2005 049 385

(51) Int. Cl.
*C07D 413/00* (2006.01)
(52) U.S. Cl. .................................................. 546/272.1
(58) Field of Classification Search ................. 546/272.1
See application file for complete search history.

(56) References Cited

FOREIGN PATENT DOCUMENTS

| WO | WO 02/14285 | 2/2002 |
|---|---|---|
| WO | WO 03/013526 | 2/2003 |
| WO | WO 03/061653 | 7/2003 |

*Primary Examiner* — Janet L. Andres
*Assistant Examiner* — Raymond Covington
(74) *Attorney, Agent, or Firm* — Serena Farquharson-Torres; Scully, Scott, Murphy & Presser, P.C.

(57) ABSTRACT

The present invention is directed to a compound of formula I:

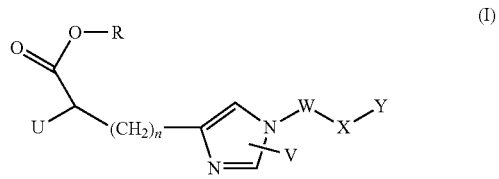

or any stereoisomeric form of the compound of the formula I or a mixture of these forms in any ratio or a physiologically acceptable salt of the compound of the formula I which inhibit the enzyme TAFIa (activated thrombin-activatable fibrinolysis inhibitor), and to a process for their preparation and to their use to treat described diseases where the substituents are as described in the specification.

6 Claims, No Drawings

IMIDAZOLE DERIVATIVES AS INHIBITORS OF TAFIA

FIELD OF THE INVENTION

The invention relates to novel compounds of the formula I which inhibit the enzyme TAFIa (activated thrombin-activatable fibrinolysis inhibitor), to a process for their preparation and to the use thereof as medicaments.

BACKGROUND OF THE INVENTION

The enzyme TAFIa is produced for example through thrombin activation from the thrombin-activatable fibrinolysis inhibitor zymogen (TAFI). The enzyme TAFI is also referred to as plasma procarboxypeptidase B, procarboxypeptidase U or procarboxypeptidase R and is a proenzyme similar to carboxypeptidase B (L. Bajzar, Arterioscler. Thromb. Vasc. Biol. 2000, pages 2511-2518).

During formation of a clot, thrombin is generated as the final product of the coagulation cascade and induces conversion of soluble plasma fibrinogen to an insoluble fibrin matrix. At the same time, thrombin activates the endogenous fibrinolysis inhibitor TAFI. Activated TAFI (TAFIa) is thus produced during thrombus formation and lysis from the zymogen TAFI through the action of thrombin; thrombomodulin in a complex with thrombin increases this effect about 1250-fold. TAFIa cleaves basic amino acids at the carboxy end of fibrin fragments. The loss of carboxy-terminal lysines as binding sites for plasminogen then leads to inhibition of fibrinolysis. Efficient inhibitors of TAFIa prevent the loss of these high-affinity lysine binding sites for plasminogen and, in this way, assist endogenous fibrinolysis by plasmin: TAFIa inhibitors have profibrinolytic effects.

In order to maintain hemostasis in the blood, mechanisms which lead to the clotting of blood and to the breaking up of clots have developed; these are in equilibrium. If a disturbed equilibrium favors coagulation, fibrin is produced in larger quantities, so that pathological processes of thrombus formation may lead to serious pathological states in humans.

Just like excessive coagulation may lead to serious pathological states caused by thrombosis, an antithrombotic treatment entails the risk of unwanted bleeding through disturbance of the formation of a necessary hemostatic plug. Inhibition of TAFIa increases endogenous fibrinolysis—without influencing coagulation and platelet aggregation—i.e. the disturbed equilibrium is shifted in favor of fibrinolysis. It is thus possible both to counter the buildup of a clinically relevant thrombus, and to increase the lysis of a pre-existing clot. On the other hand, buildup of a hemostatic plug is not impaired, so that a hemorrhagic diathesis is probably not to be expected (Bouma et al., J. Thrombosis and Haemostasis, 1, 2003, pages 1566-1574).

Inhibitors of TAFIa have previously been described in the international applications WO02/14285, WO03/013526 and WO03/061653.

The TAFIa inhibitors of the invention are suitable for a prophylactic and for a therapeutic use in humans suffering from disorders associated with thromboses, embolisms, hypercoagulability or fibrotic changes. They can be employed for secondary prevention and are suitable both for acute and for long-term therapy.

DETAILED DESCRIPTION OF THE INVENTION

The invention therefore relates to the use of a compound of the formula I

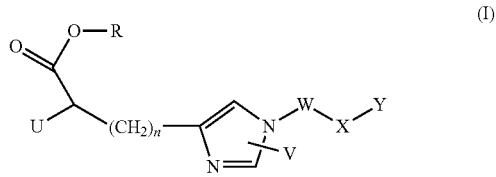

and/or any stereoisomeric form of the compound of the formula I and/or a mixture of these forms in any ratio and/or a physiologically acceptable salt of the compound of the formula I where n is an integer zero or 1, U is
1) —$(C_1$-$C_6)$-alkylene-Z,
2) —$(C_0$-$C_4)$-alkylene-$(C_3$-$C_8)$-cycloalkyl-Z,
3) —$(C_1$-$C_4)$-alkylene-Het-Z in which Het is a ring system having 4 to 15 carbon atoms which are present in one, two or three ring systems which are attached to one another and which contain one, two, three or four identical or different heteroatoms from the group consisting of oxygen, nitrogen and sulfur and in which Het is unsubstituted or mono-, di- or trisubstituted by —$(C_1$-$C_4)$-alkyl or
4) —$(C_0$-$C_2)$-alkylene-$(C_3$-$C_8)$-cycloalkyl-$(C_1$-$C_2)$—Z, where Z is a basic nitrogen-containing group, R is
1) a hydrogen atom,
2) —$(C_1$-$C_6)$-alkyl,
3) —$(C_1$-$C_6)$-alkylene-OH,
4) —$(C_0$-$C_4)$-alkylene-$(C_3$-$C_6)$-cycloalkyl,
5) —$(C_1$-$C_{10})$-alkylene-O—C(O)—O—R1,
6) —$(C_0$-$C_3)$-alkylene-$(C_6$-$C_{14})$-aryl, where aryl is unsubstituted or independently of one another mono-, di- or trisubstituted by R1, or
7) —$(C_0$-$C_3)$-alkylene-Het, where Het is as defined above and is unsubstituted or independently mono-, di- or trisubstituted by R1, V is
1) a hydrogen atom,
2) —$(C_1$-$C_4)$-alkyl,
3) halogen,
4) —$(C_6$-$C_{14})$-aryl,
5) —$NO_2$,
6) —$NH_2$,
7) —OH or
8) —$CF_3$, W is —$(C_1$-$C_4)$-alkylene, where alkylene is unsubstituted or substituted by halogen, X is an aromatic five- to thirteen-membered heterocycle whose ring systems contain 5 to 13 carbon atoms which are present in one, two or three ring systems attached to one another and which may contain one, two, three or four identical or different heteroatoms from the group consisting of oxygen, nitrogen and sulfur, where the heterocycle is unsubstituted or mono-, di- or trisubstituted independently by R1, except for the case where X is pyridyl and Y is a hydrogen atom, Y is
1) a hydrogen atom,
2) —($C_1$-$C_8$)-alkyl, where alkyl is unsubstituted or mono-, di- or trisubstituted independently by R1,
3) —($C_1$-$C_3$)-perfluoroalkyl,
4) —($C_0$-$C_4$)-alkylene-($C_3$-$C_{12}$)-cycloalkyl, where cycloalkyl is unsubstituted or mono-, di- or trisubstituted independently by R1,
5) —($C_0$-$C_4$)-alkylene-($C_6$-$C_{14}$)-aryl, where aryl is unsubstituted or mono-, di- or trisubstituted independently by R1, or
6) —($C_0$-$C_4$)-alkylene-heterocycle, where the heterocycle is an aromatic five- to thirteen-membered heterocycle whose ring systems contain 5 to 13 carbon atoms which are present in one, two or three ring systems attached to one another and which may contain one, two, three or four identical or different heteroatoms from the group consisting of oxygen, nitrogen and sulfur, where the heterocycle is unsubstituted or mono-, di- or trisubstituted independently by R1, if n is the integer zero or
Y is
1) —($C_1$-$C_3$)-perfluoroalkyl,
2) —($C_0$-$C_4$)-alkylene-($C_3$-$C_{12}$)-cycloalkyl, where cycloalkyl is unsubstituted or mono-, di- or trisubstituted independently by R1,
3) —($C_0$-$C_4$)-alkylene-($C_6$-$C_{14}$)-aryl, where aryl is unsubstituted or mono-, di- or trisubstituted independently by R1, or
4) —($C_0$-$C_4$)-alkylene-heterocycle, where the heterocycle is as defined above and the heterocycle is unsubstituted or mono-, di- or trisubstituted independently by R1, if n is the integer 1,
R1 is
1) halogen,
2) —$NO_2$,
3) —CN,
4) —N(R2)-R3, where R2 and R3 are identical or different and independently of one another are
   1) a hydrogen atom,
   2) —($C_1$-$C_6$)-alkyl,
   3) —($C_0$-$C_3$)-alkylene-($C_6$-$C_{14}$)-aryl,
   4) —($C_0$-$C_3$)-alkylene-Het, where Het is as defined above or
   5) —($C_0$-$C_3$)-alkylene-($C_3$-$C_6$)-cycloalkyl,
5) —OH,
6) —C(O)—O—R4, where R4 is
   1) a hydrogen atom,
   2) —($C_1$-$C_6$)-alkyl,
   3) —($C_0$-$C_3$)-alkylene-($C_6$-$C_{14}$)-aryl,
   4) —($C_0$-$C_3$)-alkylene-Het, where Het is as defined above or
   5) —($C_0$-$C_3$)-alkylene-($C_3$-$C_6$)-cycloalkyl,
7) —C(O)—N(R2)-R3, where R2 and R3 are identical or different and independently of one another are as defined above,
8) —O—$CF_3$,
9) —($C_0$-$C_4$)-alkylene-($C_6$-$C_{14}$)-aryl, where aryl is unsubstituted or mono-, di- or trisubstituted independently by halogen, —($C_1$-$C_4$)-alkyl, —($C_3$-$C_8$)-cycloalkyl, halogen or —O—($C_1$-$C_8$)-alkyl,
10) —($C_0$-$C_4$)-alkylene-($C_3$-$C_6$)-cycloalkyl,
11) —($C_1$-$C_8$)-alkyl, where alkyl is unsubstituted or mono-, di- or trisubstituted independently by halogen, —$NH_2$, —OH or methoxy,
12) —O—($C_1$-$C_8$)-alkyl, where alkyl is unsubstituted or mono-, di- or trisubstituted independently by halogen, —$NH_2$, —OH or methoxy,
13) —O—($C_1$-$C_4$)-alkylene-($C_6$-$C_{14}$)-aryl, where aryl is unsubstituted or mono-, di- or trisubstituted independently by halogen, —($C_1$-$C_4$)-alkyl, —($C_3$-$C_8$)-cycloalkyl, halogen or —O—($C_1$-$C_8$)-alkyl,
14) —$SO_2$—$CH_3$ or
15) —$SO_2$—$CF_3$.

The invention furthermore provides the compound of the formula I where
n is an integer zero or 1,
U is
1) —($C_1$-$C_4$)-alkylene-Z,
2) —($C_0$-$C_4$)-alkylene-($C_3$-$C_8$)-cycloalkyl-Z,
3) —($C_1$-$C_4$)-alkylene-Het-Z, where Het is selected from the group consisting of acridinyl, azepinyl, azetidinyl, benzimidazalinyl, benzimidazolyl, benzoxazolyl, benzothiazolyl, benzotriazolyl, benzotetrazolyl, benzisoxazolyl, benzisothiazolyl, carbolinyl, quinazolinyl, quinolinyl, 4H-quinolizinyl, quinoxalinyl, quinuclidinyl, cinnolinyl, decahydroquinolinyl, furazanyl, imidazolidinyl, imidazolinyl, imidazolyl, 1H-indazolyl, indolinyl, indolizinyl, indolyl, 3H-indolyl, isoindazolyl, isoindolinyl, isoindolyl, isoquinolinyl, isothiazolidinyl, 2-isothiazolinyl, isothiazolyl, isoxazolyl, isoxazolidinyl, 2-isoxazolinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, phenanthridinyl, phenanthrolinyl, phthalazinyl, pteridinyl, purinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolinyl, 2H-pyrrolyl, pyrrolyl, tetrahydroisoquinolinyl, tetrahydroquinolinyl, tetrahydropyridinyl, 6H-1,2,5-thiadazinyl, 1,2,3-thiadiazolyl, 1,2,4-thiadiazolyl, 1,2,5-thiadiazolyl, 1,3,4-thiadiazolyl, thiazolyl, thienothiazolyl, thienooxazolyl, thienoimidazolyl, thienopyridinyl, triazinyl, 1,2,3-triazolyl, 1,2,3-triazolyl, 1,2,4-triazolyl, 1,2,5-triazolyl and 1,3,4-triazolyl, where Het is unsubstituted or mono- or disubstituted by —($C_1$-$C_3$)-alkyl, —O—($C_1$-$C_3$)-alkyl or —$CF_3$ or
4) —($C_0$-$C_2$)-alkylene-($C_3$-$C_8$)-cycloalkyl-($C_1$-$C_2$)-alkylene-Z,
where Z is amino, amidino or guanidino,
R is
1) a hydrogen atom,
2) —($C_1$-$C_6$)-alkyl,
3) ($C_3$-$C_6$)-cycloalkyl,
4) —($C_1$-$C_{10}$)-alkylene-O—C(O)—O—R1 or
5) —($C_0$-$C_3$)-alkylene-($C_6$-$C_{14}$)-aryl, where aryl is selected from the group consisting of anthryl, fluorenyl, indanyl, naphthyl, phenyl and tetrahydronaphthalenyl and is unsubstituted or independently mono-, di- or trisubstituted by R1,
V is
1) a hydrogen atom,
2) —($C_1$-$C_4$)-alkyl,
3) halogen, where halogen is selected from the group consisting of fluorine, chlorine, bromine or iodine,
4) —($C_6$-$C_{14}$)-aryl, where aryl is as defined above,
5) —$NO_2$,
6) —$NH_2$,
7) —OH or
8) —$CF_3$, W is —(C$_1$-C$_4$)-alkylene, where alkylene is unsubstituted or substituted by F or Cl, X is an aromatic five- to thirteen-membered heterocycle selected from the group consisting of acridinyl, benzimidazalinyl, benzimidazolyl, benzofuranyl, benzothiofuranyl, benzothiophenyl, benzoxazolyl, benzothiazolyl, benzotriazolyl, benzotetrazolyl, benzisoxazolyl, benzisothiazolyl, carbazolyl, beta-carbolinyl, quinazolinyl, quinolizinyl, quinoxalinyl, chromanyl, chromenyl, cinnolinyl, dibenzofuranyl, dibenzothiophenyl, 2,3-dihydrobenzo[1,4]dioxin, furyl, imidazolyl, 1H-indazolyl, indolinyl, indolizinyl, indolyl, 3H-indolyl, isobenzofuranyl, isoquinolinyl, isochromanyl, isoindazolyl, isoindolinyl, isoindolyl, isothiazolidinyl, 2-isothiazolinyl, isothiazolyl, isoxazolyl, isoxazolidinyl, 2-isoxazolinyl, naphthyridinyl, oxadiazolyl, 1,2,3-oxadiazolyl, 1,2,4-oxadiazolyl, 1,2,5-oxadiazolyl, 1,3,4-oxadiazolyl, oxazolyl, phenanthridinyl, phenanthrenyl, phenazinyl, phenothiazinyl, phenoxathiinyl, phenoxazinyl, phthalazinyl, pteridinyl, purinyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridyl, pyrimidinyl, pyrrolyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazinyl, thienyl, thienothiazolyl, thienooxazolyl, thienoimidazolyl, thienopyridinyl, triazinyl, 1,2,3-triazolyl, 1,2,3-triazolyl, 1,2,4-triazolyl, 1,2,5-triazolyl, 1,3,4-triazolyl and xanthenyl, where the heterocycle is unsubstituted or mono-, di- or trisubstituted independently by R1, except for the case where X is pyridyl and Y is a hydrogen atom, Y is
1) a hydrogen atom,
2) —(C$_1$-C$_8$)-alkyl, where alkyl is unsubstituted or mono-, di- or trisubstituted independently by R1,
3) —(C$_3$-C$_8$)-cycloalkyl, where cycloalkyl is unsubstituted or mono-, di- or trisubstituted independently by R1,
4) —(C$_1$-C$_3$)-perfluoroalkyl,
5) —(C$_6$-C$_{14}$)-aryl, where aryl is as defined above and is unsubstituted or mono-, di- or trisubstituted independently by R1, or
6) —(C$_0$-C$_4$)-alkylene-heterocycle, where the heterocycle is as defined above and is unsubstituted or mono-, di- or trisubstituted independently by R1, if n is the integer zero or Y is
1) —(C$_1$-C$_3$)-perfluoroalkyl,
2) —(C$_0$-C$_4$)-alkylene-(C$_3$-C$_8$)-cycloalkyl, where cycloalkyl is unsubstituted or mono-, di- or trisubstituted independently by R1,
3) —(C$_0$-C$_4$)-alkylene-(C$_6$-C$_{14}$)-aryl, where aryl is as defined above and is unsubstituted or mono-, di- or trisubstituted independently by R1, or
4) —(C$_0$-C$_4$)-alkylene-heterocycle, where the heterocycle is as defined above and is unsubstituted or mono-, di- or trisubstituted independently by R1, if n is the integer 1, R1 is
1) halogen, where halogen is as defined above,
2) —NO$_2$,
3) —CN,
4) —N(R2)-R3, where R2 and R3 are identical or different and independently of one another are
1) a hydrogen atom,
2) —(C$_1$-C$_6$)-alkyl,
3) —(C$_0$-C$_3$)-alkylene-(C$_6$-C$_{14}$)-aryl, where aryl is as defined above,
4) —(C$_0$-C$_3$)-alkylene-Het, where Het is as defined above or
5) —(C$_0$-C$_3$)-alkylene-(C$_3$-C$_6$)-cycloalkyl,
5) —OH,
6) —C(O)—O—R4, where R4 is
1) a hydrogen atom,
2) —(C$_1$-C$_6$)-alkyl,
3) —(C$_0$-C$_3$)-alkylene-(C$_6$-C$_{14}$)-aryl, where aryl is as defined above,
4) —(C$_0$-C$_3$)-alkylene-Het, where Het is as defined above or
5) —(C$_0$-C$_3$)-alkylene-(C$_3$-C$_6$)-cycloalkyl,
7) —C(O)—N(R2)-R3, where R2 and R3 are identical or different and independently of one another are as defined above,
8) —O—CF$_3$,
9) —(C$_0$-C$_4$)-alkylene-(C$_6$-C$_{14}$)-aryl, where aryl is as defined above and is unsubstituted or mono-, di- or trisubstituted independently by halogen or —O—(C$_1$-C$_8$)-alkyl, where halogen is as defined above,
10) —(C$_0$-C$_4$)-alkylene-(C$_3$-C$_6$)-cycloalkyl,
11) —(C$_1$-C$_8$)-alkyl, where alkyl is unsubstituted or mono-, di- or trisubstituted independently by halogen, —NH$_2$, —OH or methoxy, where halogen is as defined above,
12) —O—(C$_1$-C$_8$)-alkyl, where alkyl is unsubstituted or mono-, di- or trisubstituted independently by halogen, —NH$_2$, —OH or methoxy, where halogen is as defined above,
13) —O—(C$_1$-C$_4$)-alkylene-(C$_6$-C$_{14}$)-aryl, where aryl is as defined above and is unsubstituted or mono-, di- or trisubstituted independently by halogen or —O—(C$_1$-C$_8$)-alkyl, where halogen is as defined above,
14) —SO$_2$—CH$_3$ or
15) —SO$_2$—CF$_3$.

The invention furthermore provides the compound of the formula I where U and Z together are the radical

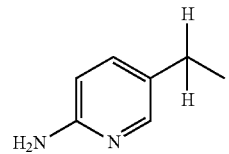

and the pyridyl moiety in the radical is unsubstituted or substituted by methyl or ethyl, n is the integer zero, R is a hydrogen atom or —(C$_1$-C$_4$)-alkyl, V is
1) a hydrogen atom,
2) —(C$_1$-C$_3$)-alkyl or
3) fluorine, chlorine or bromine, W is —(C$_1$-C$_3$)-alkylene, X is an aromatic five- to thirteen-membered heterocycle, where the heterocycle is selected from the group consisting of isoxazolyl, 1,2,3-oxadiazolyl, 1,2,4-oxadiazolyl, 1,2,5-oxadiazolyl, 1,3,4-oxadiazolyl, oxazolyl, 1,2,3-thiadiazolyl, 1,2,4-thiadiazolyl, 1,2,5-thiadiazolyl, 1,3,4-thiadiazolyl, thienopyridinyl or thienyl, and the heterocycle is unsubstituted or mono-, di- or trisubstituted independently by R1, Y is
1) a hydrogen atom,
2) —($C_1$-$C_6$)-alkyl, where alkyl is unsubstituted or mono-, di- or trisubstituted independently by R1,
3) —$CF_3$,
4) —($C_3$-$C_6$)-cycloalkyl, where cycloalkyl is unsubstituted or mono-, di- or trisubstituted independently by R1,
5) —($C_6$-$C_{14}$)-aryl, where aryl is selected from the group consisting of indanyl, naphthyl, phenyl or tetrahydronaphthalenyl, where aryl is unsubstituted or mono-, di- or trisubstituted independently by R1, or
6) a heterocycle, where the heterocycle is selected from the group consisting of 2,3-dihydrobenzo[1,4]dioxin, isoxazolyl, 1,2,3-oxadiazolyl, 1,2,4-oxadiazolyl, 1,2,5-oxadiazolyl, 1,3,4-oxadiazolyl, oxazolyl, 1,2,3-thiadiazolyl, 1,2,4-thiadiazolyl, 1,2,5-thiadiazolyl, 1,3,4-thiadiazolyl, thienopyridinyl or thienyl, and the heteroatom is unsubstituted or mono-, di- or trisubstituted independently by R1, and R1 is fluorine, chlorine, bromine, —($C_1$-$C_4$)-alkyl, —($C_0$-$C_4$)-alkylene-phenyl, —O—$CH_3$, —O—($C_1$-$C_4$)-alkylene-phenyl, where phenyl is unsubstituted or mono- or disubstituted by fluorine, chlorine, bromine or —O—($C_1$-$C_4$)-alkyl, —($C_3$-$C_6$)-cycloalkyl or —$CF_3$.

The invention furthermore provides the compound of the formula I where

U is
1) —($C_1$-$C_4$)-alkylene-Z,
2) —($C_0$-$C_4$)-alkylene-($C_3$-$C_8$)-cycloalkyl-Z or
3) —($C_0$-$C_2$)-alkylene-($C_3$-$C_8$)-cycloalkyl-($C_1$-$C_2$)-alkylene-Z, where Z is amino, amidino or guanidino,
n is the integer 1,
R is a hydrogen atom or —($C_1$-$C_4$)-alkyl, V is
1) a hydrogen atom,
2) —($C_1$-$C_3$)-alkyl or
3) fluorine, chlorine or bromine, W is —($C_1$-$C_3$)-alkylene, X is an aromatic five- to thirteen-membered heterocycle, where the heterocycle is selected from the group consisting of isoxazolyl, 1,2,3-oxadiazolyl, 1,2,4-oxadiazolyl, 1,2,5-oxadiazolyl, 1,3,4-oxadiazolyl, oxazolyl, 1,2,3-thiadiazolyl, 1,2,4-thiadiazolyl, 1,2,5-thiadiazolyl, 1,3,4-thiadiazolyl and thienopyridinyl, and the heterocycle is unsubstituted or mono-, di- or trisubstituted independently by R1, Y is
1) —($C_0$-$C_4$)-alkylene-($C_3$-$C_6$)-cycloalkyl, where cycloalkyl is unsubstituted or mono-, di- or trisubstituted independently by R1,
2) —($C_0$-$C_4$)-alkylene-phenyl, where phenyl is as defined above and is unsubstituted or mono-, di- or trisubstituted independently by R1, or
3) a heterocycle, where the heterocycle is selected from the group consisting of isoxazolyl, 1,2,3-oxadiazolyl, 1,2,4-oxadiazolyl, 1,2,5-oxadiazolyl, 1,3,4-oxadiazolyl, oxazolyl, 1,2,3-thiadiazolyl, 1,2,4-thiadiazolyl, 1,2,5-thiadiazolyl, 1,3,4-thiadiazolyl, thienopyridinyl and thienyl and the heterocycle is unsubstituted or mono-, di- or trisubstituted independently by R1, R1 is fluorine, chlorine, bromine, —O—$CH_3$ or —$CF_3$.

The invention furthermore provides compounds of the formula I from the group consisting of
3-(6-aminopyridin-3-yl)-2-{1-[5-(5-chlorothiophen-2-yl) isoxazol-3-ylmethyl]-1H-imidazol-4-yl}propionic acid,
3-(6-aminopyridin-3-yl)-2-[1-(5-phenylisoxazol-3-ylmethyl)-1H-imidazol-4-yl]propionic acid,
3-(6-aminopyridin-3-yl)-2-{1-[2-(5-chlorothiophen-2-yl) thiazol-5-ylmethyl]-1H-imidazol-4-yl}propionic acid,
3-(6-aminopyridin-3-yl)-2-[1-(6-chlorothieno[2,3-b]pyridin-2-ylmethyl)-1H-imidazol-4-yl]propionic acid,
3-(6-aminopyridin-3-yl)-2-{1-[5-(4-methoxyphenyl)isoxazol-3-ylmethyl]-1H-imidazol-4-yl}propionic acid,
3-(6-aminopyridin-3-yl)-2-{1-[5-(3-methylbutyl)isoxazol-3-ylmethyl]-1H-imidazol-4-yl}propionic acid,
3-(6-aminopyridin-3-yl)-2-{1-[5-(5-chlorothiophen-2-yl)-[1,3,4]thiadiazol-2-ylmethyl]-1H-imidazol-4-yl}propionic acid,
3-(6-aminopyridin-3-yl)-2-{1-[5-(4-chlorophenyl)-[1,3,4]thiadiazol-2-ylmethyl]-1H-imidazol-4-yl}propionic acid,
3-(6-aminopyridin-3-yl)-2-[1-(5-tert-butyl-[1,3,4]thiadiazol-2-ylmethyl)-1H-imidazol-4-yl]propionic acid,
3-(6-aminopyridin-3-yl)-2-{1-[5-(4-trifluoromethylphenyl)-[1,2,4]oxadiazol-3-ylmethyl]-1H-imidazol-4-yl}propionic acid,
3-(6-aminopyridin-3-yl)-2-{1-[5-(3-trifluoromethylphenyl)-[1,2,4]oxadiazol-3-ylmethyl]-1H-imidazol-4-yl}propionic acid,
3-(6-aminopyridin-3-yl)-2-[1-(5-cyclopropyl-[1,3,4]thiadiazol-2-ylmethyl)-1H-imidazol-4-yl]propionic acid,
3-(6-aminopyridin-3-yl)-2-[1-(5-phenyl-[1,2,4]oxadiazol-3-ylmethyl)-1H-imidazol-4-yl]propionic acid,
3-(6-aminopyridin-3-yl)-2-{1-[3-(3,4-dimethoxyphenyl)-[1,2,4]oxadiazol-5-ylmethyl]-1H-imidazol-4-yl}propionic acid,
3-(6-aminopyridin-3-yl)-2-{1-[3-(4-methoxyphenyl)-[1,2,4]oxadiazol-5-ylmethyl]-1H-imidazol-4-yl}propionic acid,
3-(6-aminopyridin-3-yl)-2-{1-[3-(4'-isopropylphenyl)-[1,2,4]oxadiazol-5-ylmethyl]-1H-imidazol-4-yl}propionic acid,
3-(6-aminopyridin-3-yl)-2-{1-[3-(4'-tert-butylphenyl)-[1,2,4]oxadiazol-5-ylmethyl]-1H-imidazol-4-yl}propionic acid,
3-(6-aminopyridin-3-yl)-2-{1-[5-(2-methylthiazol-4-yl) isoxazol-3-ylmethyl]-1H-imidazol-4-yl}propionic acid,
3-(6-aminopyridin-3-yl)-2-{1-[5-(3,4-dichlorophenyl)isoxazol-3-ylmethyl]-1H-imidazol-4-yl}propionic acid,
3-(6-aminopyridin-3-yl)-2-{1-[3-(4-methoxyphenyl)-[1,2,4]oxadiazol-5-ylmethyl]-1H-imidazol-4-yl}propionic acid,
3-(6-aminopyridin-3-yl)-2-[1-(5-phenyl-[1,3,4]thiadiazol-2-ylmethyl)-1H-imidazol-4-yl]propionic acid,
3-(6-aminopyridin-3-yl)-2-{1-[5-(4-methoxyphenyl)-[1,3,4]thiadiazol-2-ylmethyl]-1H-imidazol-4-yl}propionic acid,
3-(6-aminopyridin-3-yl)-2-{1-[5-(3,5-dimethylisoxazol-4-yl)-[1,2,4]oxadiazol-3-ylmethyl]-1H-imidazol-4-yl}propionic acid,
3-(6-aminopyridin-3-yl)-2-[1-(5-thiophen-2-yl isoxazol-3-ylmethyl)-1H-imidazol-4-yl]propionic acid,
3-(6-aminopyridin-3-yl)-2-[1-(5-tert-butyl-1,2,4-oxadiazol-3-ylmethyl)-1H-imidazol-4-yl]propionic acid,
3-(6-aminopyridin-3-yl)-2-(1-{3-[4-(4-chlorobenzyloxy) phenyl]-[1,2,4]oxadiazol-5-ylmethyl}-1H-imidazol-4-yl) propionic acid,
3-(6-aminopyridin-3-yl)-2-[1-(4-bromothiophen-2-ylmethyl)-1H-imidazol-4-yl]propionic acid,
3-(6-aminopyridin-3-yl)-2-[1-(5-methyl isoxazol-3-ylmethyl)-1H-imidazol-4-yl]propionic acid,
3-(6-aminopyridin-3-yl)-2-[1-(4-phenyl-5-trifluoromethylthiophen-2-ylmethyl)-1H-imidazol-4-yl]propionic acid,
3-(6-aminopyridin-3-yl)-2-{1-[5-(4-bromophenyl)isoxazol-3-ylmethyl]-1H-imidazol-4-yl}propionic acid, 3-(6-aminopyridin-3-yl)-2-[1-(5-p-tolylisoxazol-3-ylm-ethyl)-1H-imidazol-4-yl]propionic acid,
3-(6-aminopyridin-3-yl)-2-(1-{2-[5-(5-chlorothiophen-2-yl)isoxazol-3-yl]-ethyl}-1H-imidazol-4-yl)propionic acid,
3-(6-aminopyridin-3-yl)-2-{1-[5-(4-isobutylphenyl)isox-azol-3-ylmethyl]-1H-imidazol-4-yl}propionic acid,
3-(6-aminopyridin-3-yl)-2-[1-(5-cyclopentyl-[1,3,4]thiadia-zol-2-ylmethyl)-1H-imidazol-4-yl]propionic acid,
3-(6-aminopyridin-3-yl)-2-[1-(5-cyclobutyl-[1,3,4]thiadia-zol-2-ylmethyl)-1H-imidazol-4-yl]propionic acid,
3-(6-aminopyridin-3-yl)-2-[1-(5-cyclopropyl isoxazol-3-yl-methyl)-1H-imidazol-4-yl]propionic acid,
3-(6-aminopyridin-3-yl)-2-[1-(5-cyclohexyl isoxazol-3-yl-methyl)-1H-imidazol-4-yl]propionic acid,
3-(6-aminopyridin-3-yl)-2-[1-(5-cyclohexyl-[1,3,4]thiadia-zol-2-ylmethyl)-1H-imidazol-4-yl]propionic acid,
3-(6-aminopyridin-3-yl)-2-{1-[5-(3-methylbutyl)-[1,3,4]thiadiazol-2-ylmethyl]-1H-imidazol-4-yl}propionic acid,
3-(6-aminopyridin-3-yl)-2-[1-(5-cyclobutyl isoxazol-3-ylm-ethyl)-1H-imidazol-4-yl]propionic acid,
3-(6-aminopyridin-3-yl)-2-{1-[5-(4-fluorophenyl)isoxazol-3-ylmethyl]-1H-imidazol-4-yl}propionic acid,
3-(6-aminopyridin-3-yl)-2-{1-[5-(4-benzylphenyl)isoxazol-3-ylmethyl]-1H-imidazol-4-yl}propionic acid,
3-(6-aminopyridin-3-yl)-2-{1-[5-(4-tert-butylphenyl)isox-azol-3-ylmethyl]-1H-imidazol-4-yl}propionic acid,
3-(6-aminopyridin-3-yl)-2-{1-[5-(4-tert-butyl-2,6-dimethyl phenyl)isoxazol-3-ylmethyl]-1H-imidazol-4-yl}propionic acid,
3-(6-aminopyridin-3-yl)-2-{1-[5-(2-chlorophenyl)isoxazol-3-ylmethyl]-1H-imidazol-4-yl}propionic acid,
3-(6-aminopyridin-3-yl)-2-{1-[5-(4-sec-butylphenyl)isox-azol-3-ylmethyl]-1H-imidazol-4-yl}propionic acid,
3-(6-aminopyridin-3-yl)-2-[1-(5-indan-5-ylisoxazol-3-ylm-ethyl)-1H-imidazol-4-yl]propionic acid,
3-(6-aminopyridin-3-yl)-2-{1-[5-(4-cyclopentylphenyl)isoxazol-3-ylmethyl]-1H-imidazol-4-yl}propionic acid,
3-(6-aminopyridin-3-yl)-2-{1-[5-(4-isopropylphenyl)isox-azol-3-ylmethyl]-1H-imidazol-4-yl}propionic acid,
3-(6-aminopyridin-3-yl)-2-{1-[5-(4-butylphenyl)isoxazol-3-ylmethyl]-1H-imidazol-4-yl}propionic acid,
3-(6-aminopyridin-3-yl)-2-{1-[5-(4-cyclohexylphenyl)isox-azol-3-ylmethyl]-1H-imidazol-4-yl}propionic acid,
3-(6-aminopyridin-3-yl)-2-{1-[5-(5,6,7,8-tetrahydronaph-thalen-2-yl)isoxazol-3-ylmethyl]-1H-imidazol-4-yl}propionic acid,
3-(6-aminopyridin-3-yl)-2-{1-[5-(4-propyl phenyl)isoxazol-3-ylmethyl]-1H-imidazol-4-yl}propionic acid,
3-(6-aminopyridin-3-yl)-2-{1-[5-(4-phenethylphenyl)isox-azol-3-ylmethyl]-1H-imidazol-4-yl}propionic acid,
3-(6-aminopyridin-3-yl)-2-{1-[5-(2,3-dihydrobenzo[1,4]di-oxin-6-yl)isoxazol-3-ylmethyl]-1H-imidazol-4-yl}propionic acid,
ethyl (S)-3-(6-aminopyridin-3-yl)-2-{1-[5-(5-chlo-rothiophen-2-yl)isoxazol-3-ylmethyl]-1H-imidazol-4-yl}propionate,
ethyl (R)-3-(6-aminopyridin-3-yl)-2-{1-[5-(5-chlo-rothiophen-2-yl)isoxazol-3-ylmethyl]-1H-imidazol-4-yl}propionate,
(S)-3-(6-aminopyridin-3-yl)-2-{1-[5-(5-chlorothiophen-2-yl)isoxazol-3-ylmethyl]-1H-imidazol-4-yl}propionic acid,
(R)-3-(6-aminopyridin-3-yl)-2-{1-[5-(5-chlorothiophen-2-yl)isoxazol-3-ylmethyl]-1H-imidazol-4-yl}propionic acid,
6-amino-2-[1-(5-cyclopropyl-[1,3,4]thiadiazol-2-ylmethyl)-1H-imidazol-4-yl]hexanoic acid,
3-(6-amino-5-methylpyridin-3-yl)-2-[1-(5-cyclopropyl-[1,3,4]thiadiazol-2-ylmethyl)-1H-imidazol-4-yl]propionic acid,
3-(4-aminocyclohexyl)-2-[1-(5-cyclopropyl-[1,3,4]thiadia-zol-2-ylmethyl)-1H-imidazol-4-yl]propionic acid or
3-(4-aminocyclohexyl)-2-[1-(5-cyclopropyl-[1,3,4]thiadia-zol-2-ylmethyl)-1H-imidazol-4-yl]propionic acid.

The terms "$(C_1-C_4)$-alkyl" and "$(C_2-C_8)$-alkyl" are to be understood as meaning hydrocarbon radicals whose carbon chain is straight-chain or branched and comprises 1 to 4 carbon atoms and 2 to 8 carbon atoms, respectively, for example methyl, ethyl, propyl, isopropyl, butyl, isobutyl, tertiary butyl, pentyl, isopentyl, neopentyl, hexyl, 2,3-dimethylbutanyl, neohexyl, heptyl or octanyl.

The term "—$(C_0-C_4)$-alkylene" is understood as meaning hydrocarbon radicals whose carbon chain is straight-chain or branched and comprises 1 to 4 carbon atoms, for example methylene, ethylene, propylene, isopropylene, isobutylene, butylene or tertiary butylene. "—$C_0$-Alkylene" is a covalent bond.

The term "—$(C_1-C_4)$-alkylene" is understood as meaning hydrocarbon radicals whose carbon chain is straight-chain or branched and comprises 1 to 4 carbon atoms, for example methylene (—CH$_2$—), ethylene (—CH$_2$—CH$_2$—), propylene (—CH$_2$—CH$_2$—CH$_2$—), isopropylene, isobutylene, butylene or tertiary butylene.

These alkylene radicals for the radical W link the nitrogen atom in the imidazole ring to the radical X.

The term "$(C_3-C_{12})$-cycloalkyl" is understood as meaning radicals such as compounds derived from 3- to 8-membered mono-, bi- or tricycles or bridged rings such as the monocycles cyclopropane, cyclobutane, cyclopentane, cyclohexane, cycloheptane or cyclooctane, derived from the bicycles bicyclo[4.2.0]octane, octahydroindene, decahydronaphthalene, decahydroazulene, decahydrobenzocycloheptene or dodecahydroheptalene, or derived from the bridged rings such as spiro[2.5]octane, spiro[3.4]octane, spiro[312.5]nonane, bicyclo[3.1.1]heptane, bicyclo[2.2.1]heptane or bicyclo[2.2.2]octane.

The term "—$(C_6-C_{14})$-aryl" is understood as meaning aromatic carbon radicals having 6 to 14 carbon atoms in the ring. Examples of —$(C_6-C_{14})$-aryl radicals are anthryl, fluorenyl, indanyl, for example 1-naphthyl, 2-naphthyl, phenyl or tetrahydronaphthalenyl. Indanyl-, tetrahydronaphthanlenyl- and especially phenyl radicals are preferred aryl radicals.

The term "aromatic five- to thirteen-membered heterocycle" is understood as meaning ring systems having 5 to 13 carbon atoms which are present in one, two or three ring systems which are linked to one another and which may contain one, two, three or four identical or different heteroatoms from the group consisting of oxygen, nitrogen and sulfur. Examples of these ring systems are the radicals acridinyl, azepinyl, azetidinyl, benzimidazalinyl, benzimidazolyl, benzofuranyl, benzothiofuranyl, benzothiophenyl, benzoxazolyl, benzothiazolyl, benzotriazolyl, benzotetrazolyl, benzisoxazolyl, benzisothiazolyl, carbazolyl, beta-carbolinyl, quinazolinyl, quinolizinyl, quinoxalinyl, chromanyl, chromenyl, cinnolinyl, dibenzofuranyl, dibenzothiophenyl, 2,3-dihydrobenzo[1,4]dioxin, dioxolenyl, furanyl, imidazolidinyl, imidazolinyl, imidazolyl, 1H-indazolyl, indolinyl, indolizinyl, indolyl, 3H-indolyl, isobenzofuranyl, isoquinolinyl (benzimidazolyl), isochromanyl, isoindazolyl, isoindolinyl, isoindolyl, isothiazolidinyl, 2-isothiazolinyl, isothiazolyl, isoxazolyl, isoxazolidinyl, 2-isoxazolinyl, naphthyridinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxothiolanyl, phenanthridinyl, phenanthrenyl, phenazinyl, phenothiazinyl, phenoxathiinyl, phenoxazinyl, phthalazinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridothiophenyl, pyridyl, pyrimidinyl, pyrrolinyl, pyrrolyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazinyl, thienyl, thienoimidazolyl, thienooxazolyl, thienopyridinyl, thienothiazolyl, thiopyranyl, triazinyl, 1,2,3-triazolyl, 1,2,3-triazolyl, 1,2,4-triazolyl, 1,2,5-triazolyl, 1,3,4-triazolyl and xanthenyl.

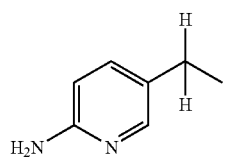

The radical is understood as meaning 5-methylenepyridin-2-ylamine where the pyridine is attached via the methylene radical to the radical of the compound of the formula I. The term "Het" is understood as meaning ring systems having 4 to 15 carbon atoms which are present in one, two or three ring systems which are linked to one another and which may contain one, two, three or four identical or different heteroatoms from the group consisting of oxygen, nitrogen and sulfur. Examples of these ring systems are the radicals acridinyl, azepinyl, azetidinyl, benzimidazolinyl, benzimidazolyl, benzoxazolyl, benzothiazolyl, benzotriazolyl, benzotetrazolyl, benzisoxazolyl, benzisothiazolyl, carbolinyl, quinazolinyl, quinolinyl, 4H-quinolizinyl, quinoxalinyl, quinuclidinyl, cinnolinyl, decahydroquinolinyl, furazanyl, imidazolidinyl, imidazolinyl, imidazolyl, 1H-indazolyl, indolinyl, indolizinyl, indolyl, 3H-indolyl, isoindazolyl, isoindolinyl, isoindolyl, isoquinolinyl, isothiazolidinyl, 2-isothiazolinyl, isothiazolyl, isoxazolyl, isoxazolidinyl, 2-isoxazolinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, phenanthridinyl, phenanthrolinyl, phthalazinyl, pteridinyl, purinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolinyl, 2H-pyrrolyl, pyrrolyl, tetrahydroisoquinolinyl, tetrahydroquinolinyl, tetrahydropyridinyl, 6H-1,2,5-thiadazinyl, 1,2,3-thiadiazolyl, 1,2,4-thiadiazolyl, 1,2,5-thiadiazolyl, 1,3,4-thiadiazolyl, thiazolyl, thienothiazolyl, thienooxazolyl, thienoimidazolyl, thienopyridin, triazinyl, 1,2,3-triazolyl, 1,2,3-triazolyl, 1,2,4-triazolyl, 1,2,5-triazolyl and 1,3,4-triazolyl. Preferred Het rings are the radicals isoxazolyl, 1,2,3-oxadiazolyl, 1,2,4-oxadiazolyl, 1,2,5-oxadiazolyl, 1,3,4-oxadiazolyl, oxazolyl, 1,2,3-thiadiazolyl, 1,2,4-thiadiazolyl, 1,2,5-thiadiazolyl, 1,3,4-thiadiazolyl and thienopyridinyl.

The term "—($C_1$-$C_3$)-perfluoroalkyl" is understood as meaning a partially or fully fluorinated alkyl radical derived, for example, from the following radicals —$CF_3$, —$CHF_2$, —$CH_2F$, —$CHF$—$CF_3$, —$CHF$—$CHF_2$, —$CHF$—$CH_2F$, —$CH_2$—$CF_3$, —$CH_2$—$CHF_2$, —$CH_2$—$CH_2F$, —$CF_2$—$CF_3$, —$CF_2$—$CHF_2$, —$CF_2$—$CH_2F$, —$CH_2$—$CHF$—$CF_3$, —$CH_2$—$CHF$—$CHF_2$, —$CH_2$—$CHF$—$CH_2F$, —$CH_2$—$CH_2$—$CF_3$, —$CH_2$—$CH_2$—$CHF_2$, —$CH_2$—$CH_2$—$CH_2F$, —$CF_2$—$CF_2$—$CF_3$, —$CF_2$—$CF_2$—$CHF_2$, —$CF_2$—$CF_2$—$CH_2F$, —$CHF$—$CHF$—$CF_3$, —$CHF$—$CHF$—$CHF_2$, —$CHF$—$CHF$—$CH_2F$, —$CHF$—$CH_2$—$CF_3$, —$CHF$—$CH_2$—$CH_2F$, —$CHF$—$CF_2$—$CF_3$, —$CHF$—$CF_2$—$CHF_2$, —$CHF$—$CF_2$—$CH_2F$, —$CF_2$—$CHF$—$CF_3$, —$CF_2$—$CHF$—$CHF_2$, —$CF_2$—$CHF$—$CH_2F$, —$CF_2$—$CH_2$—$CF_3$, —$CF_2$—$CH_2$—$CHF_2$, —$CF_2$—$CH_2$—$CH_2F$, —$CF_2$—$CF_2$—$CF_3$, —$CF_2$—$CF_2$—$CHF_2$ or —$CF_2$—$CF_2$—$CH_2F$.

The term "halogen" is understood as meaning fluorine, chlorine, bromine or iodine, preferably fluorine, chlorine or bromine, especially chlorine or bromine.

The term "a basic nitrogen-containing group" is understood as meaning radicals where the conjugated acid of this group has a pKa of approximately 5 to 15. Examples of this basic nitrogen-containing group are amino, amidino (carbamimidoyl), guanidino, azetidinyl, pyrrolidinyl, piperidinyl, pyridinyl or aminopyridinyl.

The compounds according to the invention can be prepared by well-known processes or by the processes described herein.

Functional groups of the intermediates used, for example amino or carboxyl groups such as the —COOR radical in the compound of the formula I, can be masked here by suitable protective groups. Suitable protective groups for amino functions are, for example, the t-butoxycarbonyl, the benzyloxycarbonyl or the phthaloyl group, and also the trityl or tosyl protective group. Suitable protective groups for the carboxyl function are, for example, alkyl, aryl or arylalkyl esters. Protective groups can be introduced and removed by techniques which are well-known or described here (see Green, T. W., Wutz, P. G. M., *Protective Groups in Organic Synthesis* (1991), 2nd Ed., Wiley-Interscience, or Kocienski, P., *Protecting Groups* (1994), Thieme). The term protective group can also include polymer-bound protective groups. Such masked compounds according to formula (I), in which, for example, the functional groups of the radicals U, V, X or W can optionally also be masked, can, although optionally themselves not pharmacologically active, optionally be converted after administration to mammals by metabolization to the pharmacologically active compounds according to the invention.

The invention furthermore relates to a process for the preparation of the compound of the formula I and/or a stereoisomeric form of the compound of the formula I and/or a physiologically acceptable salt of the compound of the formula I, where in formula I in each case n=0, wherein the compound of the formula I is prepared according to Scheme 1, where R, U, V, W, X and Y each have the meanings given above and LG is a suitable leaving group, such as —Cl, —Br, —I, —O-tosyl or —O-mesyl:

Scheme 1:

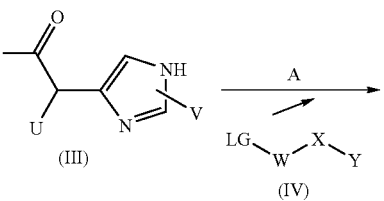

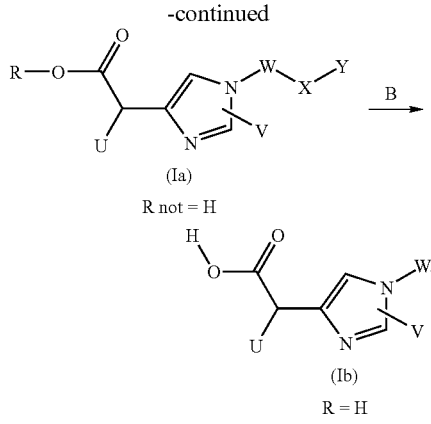

In a process step A, the compound of the formula III is dissolved in a polar aprotic solvent such as dimethylformamide (DMF) or tetrahydrofuran (THF), deprotonated with a suitable base such as sodium hydride or lithium hexamethyldisilazane and reacted with compounds of the formula IV. In a process step B, the compounds Ia obtained can be converted by suitable removal of the ester group where R is not H (cf., for example, Kocienski, P. J., *Protecting groups*, Thieme 1994) into the compounds Ib where R=H. The invention furthermore relates to a process for preparing the compound of the formula I and/or a stereoisomeric form of the compound of the formula I and/or a physiologically acceptable salt of the compound of the formula I, where in formula I in each case n=1, wherein the compound of the formula I is prepared according to Scheme 2, where R, U, V, W, X and Y each have the meanings given above and LG is a suitable leaving group, such as —Cl, —Br, —I, —O-tosyl or —O-mesyl:

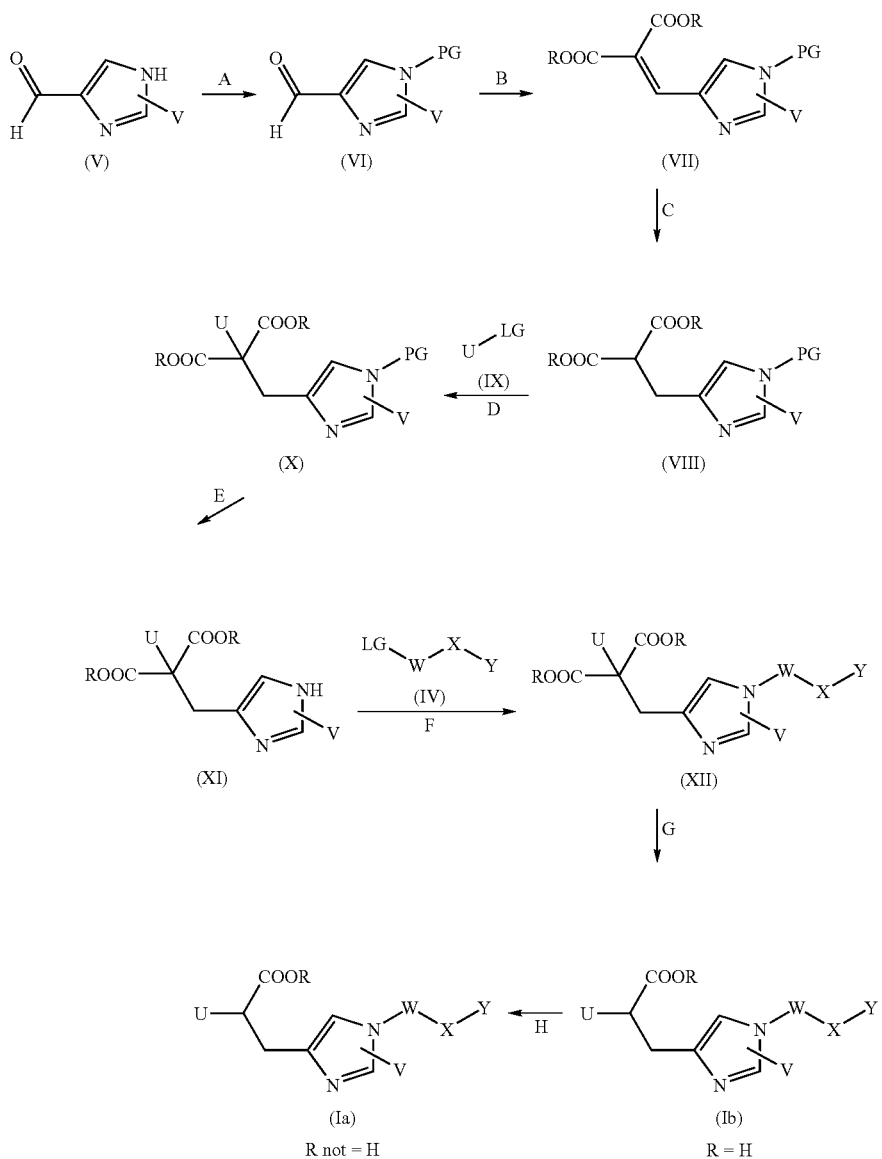

In this process according to Scheme 2, compounds of the formula V are, in step A, provided with a suitable imidazole protective group known from the literature. Suitable protective groups PG used are preferably the nitrogen protective groups customary in peptide chemistry, for example protective groups of the urethane type, such as benzyloxycarbonyl (Z), t-butyloxycarbonyl (Boc), 9-fluorenylmethoxycarbonyl (Fmoc) and allyloxycarbonyl (Aloc), or of the acid amide type, in particular formyl, acetyl or trifluoroacetyl, of the alkyl type, such as benzyl, or of the silyl type, in particular 2-(trimethylsilyl)ethoxymethyl (SEM) (P. Kociénski, Protecting Groups, Thieme Verlag 1994). Particularly suitable are also protective groups of the sulfonamide type, such as p-tosyl (Ts) or mesyl (Ms) (for example analogously to Helferich, B.; Boshagen, H.; Chem Ber 1959, 92, 2813). The amino protective group PG is introduced by methods as described in Houben-Weyl "Methoden der Org. Chemie" [Methods of Organic Chemistry], volume 15/1.

In process step B, the resulting compounds of the formula VI are converted by Knoevenagel condensation (Organikum, VCH-Wiley, 22. edition 2004, p. 527ff) with a malonic ester derivative into compounds of the formula VII. Process step C comprises the hydrogenation of compounds of the formula VII to compounds of the formula VIII by hydrogen transfer in a polar protic solvent, such as, for example, methanol or ethanol, if appropriate with addition of a base with the aid of a suitable transition metal catalyst, such as, for example, palladium on carbon. In a process step D, the compound of the formula VIII is dissolved in a polar aprotic solvent, such as dimethylformamide or tetrahydrofuran, deprotonated with a suitable base, such as sodium hydride, lithium hexamethyldisilazane or potassium carbonate and reacted with compounds of the formula IX in which LG has the meanings given above. Process step E comprises the removal of the imidazole protective group PG in formula X according to processes customary in literature, giving compounds of the formula XI. In a process step F, the compound of the formula XI is dissolved in a polar aprotic solvent, such as dimethylformamide or tetrahydrofuran, deprotonated with a suitable base, such as sodium hydride or lithium hexamethyldisilazane and reacted with compounds of the formula IV in which LG has the meanings given above. Process step G comprises the removal of the ester groups —COOR and the decarboxylation according to the literature of the malonic acid derivative formed in aqueous acidic media, if appropriate at elevated temperatures, and also, if appropriate, complete or partial removal of any of the protective groups present in U, V, W, X and Y from the compounds according to formula XII to give compounds of the formula Ib in which R is a hydrogen atom. Compounds of the formula Ia in which R is not hydrogen can be generated by process step H via esterification processes customary in literature.

The invention furthermore relates to a process for preparing the compound of the formula I and/or a stereoisomeric form of the compound of the formula I and/or a physiologically acceptable salt of the compound of the formula I, where in formula I in each case n=0, wherein the compound of the formula I is prepared according to Scheme 3, where PG, R, U, V, W, X and Y each have the meanings given above and LG is a suitable leaving group, such as —Cl, —Br, —I, —O-tosyl or —O-mesyl:

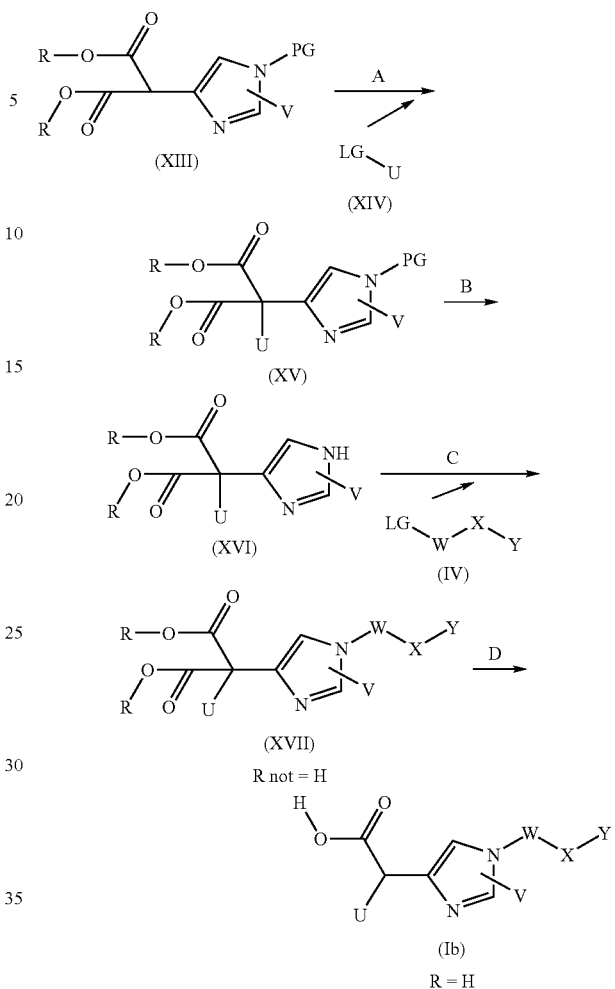

In a process step A, the compound of the formula XIII is dissolved in a polar aprotic solvent, such as dimethylformamide (DMF) or tetrahydrofuran (THF), deprotonated with a suitable base, such as cesium carbonate, sodium hydride or lithium hexamethyldisilazane and reacted with compounds of the formula XIV. Process step B comprises the removal of the imidazole protective group PG in formula XV according to a process customary in literature to give compounds of the formula XVI. In a process step C, the compound of the formula XVI is dissolved in a polar aprotic solvent, such as dimethylformamide (DMF) or tetrahydrofuran (THF), reacted with a suitable base, such as cesium carbonate, sodium hydride or lithium hexamethyldi-silazane and reacted with compounds of the formula IV. Process step D comprises ester removal and decarboxylation according to processes customary in literature, for example by heating in aqueous acids or bases.

The synthesis of compounds of the formula III can be carried out analogously to the process described in *J. Med. Chem.* 2003, 46, 5294-5297. The preparation of the compound of the formula IV is carried out by known processes and can be carried out, for example, analogously to the methods described in Ewing, William R. et al. PCT Int. Appl. (2001), 460 pp. WO 0107436 A2 or in *Bioorg. Med. Chem. Lett.* 2004, 14, 4191-4195. 2-Bromomethyl-6-chlorothieno [2,3-b]pyridine can be obtained by the above processes from 6-chlorothieno[2,3-b]pyridine-2-carbaldehyde, described in

*Journal of the Chemical Society, Perkin Transactions* 1: Organic and Bio-Organic Chemistry 1981, 9, 2509-17.

The reactions can be carried out at atmospheric, elevated or reduced pressure. In general, they are carried out at atmospheric pressure.

Suitable solvents for process steps (A) and (B) in Scheme 1 and for process steps (D) and (F) in Scheme 2 and (A) and (C) in Scheme 3 are inert organic solvents. These include, for example, ethers, such as dioxane, THF or 1,2-dimethoxyethane, hydrocarbons, such as cyclohexane, benzene, toluene or xylene, nitroaromatics, such as nitrobenzene, carboxamides, such as dimethylformamide or dimethylacetamide, alkyl sulfoxides, such as dimethyl sulfoxide, aliphatic nitriles, such as acetonitrile, or other solvents, such as N-methylpyrrolidinone. For process steps (A), (B), (E) and (H) in Scheme 2, in addition to the solvents mentioned, it is also possible to use halogenated hydrocarbons, such as dichloromethane, chloroform and dichloroethane. Preferred solvents for step (C) in Scheme 2 and step (B) in Scheme 3 are lower aliphatic alcohols, such as methanol or ethanol. Suitable for steps (G) and (D) in Scheme 3 are aqueous acid-containing solvent mixtures. It is also possible to use mixtures of the respective solvents mentioned.

Suitable bases for process steps (A) and (B) in Scheme 1 and (A), (B), (C), (D), (E), (F) and (H) in Scheme 2 and (A) and (C) in Scheme 3 are the customary inorganic and organic bases. These preferably include alkali metal and alkaline earth metal carbonates, such as sodium carbonate, potassium carbonate or calcium carbonate, alkali metal hydrides, such as sodium hydride, amides, such as lithium bis(trimethylsilyl)amide or lithium diisopropylamide, organic amines, such as pyridine, 4-N,N-dimethylaminopyridine, triethylamine, ethyldiisopropylamine, N-methylmorpholine, N-methylpiperidine, 1,5-diazabicyclo[4.3.0]non-5-ene (DBN) or 1,8-diazabicyclo[5.4.0]undec-7-ene (DBU), or organometallic compounds, such as butyllithium or phenyllithium. Particular preference is given to sodium hydride, lithium bis(trimethylsilyl)amide and triethylamine.

A compound of the formula I prepared as in Scheme 1, or a suitable precursor of the formula I which occurs in enantiomeric form owing to its chemical structure, can be fractionated by salt formation with enantiopure acids or bases, chromatography on chiral stationary phases or derivatization by means of chiral enantiopure compounds such as amino acids, separation of the diastereomers obtained in this way, and elimination of the chiral auxiliary groups into the pure enantiomers (process b), or the compound of the formula I prepared as in Scheme 1 can either be isolated in free form or be converted into physiologically tolerated salts in the case where acetic or basic groups are present (process d).

In process step c), the compound of the formula I, if it occurs as mixture of diastereomers or enantiomers, or results as mixtures thereof in the chosen synthesis, is separated into the pure stereoisomers, either by chromatography on an optionally chiral support material or, if the racemic compound of the formula I is able to form salts, by fractional crystallization of the diastereomeric salts formed with an optically active base or acid as auxiliary. Examples of suitable chiral stationary phases for thin-layer or column chromatographic separation of enantiomers are modified silica gel supports (called Pirkle phases) and high molecular weight carbohydrates such as triacetylcellulose. For analytical purposes it is also possible to use gas chromatography methods, after appropriate derivatization known to the skilled worker, on chiral stationary phases. To separate enantiomers of the racemic carboxylic acids, diastereomeric salts differing in solubility are formed with an optically active, usually commercially available base such as (−)-nicotine, (+)- and (−)-phenylethylamine, quinine bases, L-lysine or L- and D-arginine, the less soluble component is isolated as solid, the more soluble diastereomer is deposited from the mother liquor, and the pure enantiomers are obtained from the diastereomeric salts obtained in this way. It is possible in the same way in principle to convert the racemic compounds of the formula I comprising a basic group such as an amino group with optically active acids such as (+)-camphor-10-sulfonic acid, D- and L-tartaric acid, D- and L-lactic acid, and (+) and (−)-mandelic acid into the pure enantiomers. Chiral compounds comprising alcohol or amine functions can also be converted with appropriately activated or optionally N-protected enantiopure amino acids into the corresponding esters or amides, or conversely chiral carboxylic acids can be converted with carboxy-protected enantiopure amino acids into the amides, or with enantiopure hydroxy carboxylic acids such as lactic acid into the corresponding chiral esters. The chirality of the amino acid or alcohol residue introduced in enantiopure form can then be utilized for separating the isomers by carrying out a separation of the diastereomers now present by crystallization or chromatography on suitable stationary phases, and then eliminating the included chiral moiety again by suitable methods.

A further possibility with some of the compounds of the invention is to employ diastereomerically or enantiomerically pure starting materials to prepare the framework structures. It is thus possible where appropriate also to employ other or simplified processes for purifying the final products. These starting materials have previously been prepared enantiomerically or diastereomerically pure by processes known from the literature. This may mean in particular that either enantioselective processes are employed in the synthesis of the basic structures, or else a separation of enantiomers (or diastereomers) is carried out at an early stage of the synthesis and not at the stage of the final products. A simplification of these separations can likewise be achieved by proceeding in two or more stages.

Acidic or basic products of the compound of the formula I may be in the form of their salts or in free form. Pharmacologically acceptable salts are preferred, for example alkali metal or alkaline earth metal salts such as hydrochlorides, hydrobromides, sulfates, hemisulfates, all possible phosphates, and salts of amino acids, natural bases or carboxylic acids. Physiologically tolerated salts are prepared from compounds of the formula I able to form salts, including their stereoisomeric forms, in step c) of the process in a manner known per se. The compounds of the formula I form stable alkali metal, alkaline earth metal or, where appropriate, substituted ammonium salts with basic reagents such as hydroxides, carbonates, bicarbonates, alcoholates and ammonia or organic bases, for example trimethyl- or triethylamine, ethanolamine, diethanolamine or triethanolamine, trometamol or else basic amino acids, for example lysine, ornithine or arginine. If the compounds of the formula I have basic groups, it is also possible to prepare stable acid addition salts with strong acids. Suitable for this purpose are both inorganic and organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic, or trifluoroacetic acid.

The invention also relates to medicaments characterized by an effective content of at least one compound of the formula I and/or of a physiologically tolerated salt of the compound of the formula I and/or an optionally stereoisomeric form of the compound of the formula I, together with a pharmaceutically suitable and physiologically tolerated carrier, additive and/or further active ingredients and excipients.

By reason of the pharmacological properties, the compounds of the invention are suitable for the prophylaxis, secondary prevention and therapy of all disorders which can be treated by inhibition of TAFIa. Thus, TAFIa inhibitors are suitable both for a prophylactic and for a therapeutic use in humans. They are suitable both for an acute treatment and for a long-term therapy. TAFIa inhibitors can be employed in patients suffering from impairments of wellbeing or diseases associated with thromboses, embolisms, hypercoagulability or fibrotic changes.

These include myocardial infarction, angina pectoris and all other types of acute coronary syndrome, stroke, peripheral vascular disorders, deep vein thrombosis, pulmonary embolism, embolic or thrombotic events caused by cardiac arrhythmias, cardiovascular events such as restenosis following revascularization, angioplasty and similar procedures such as stent implantations and bypass operations. TAFIa inhibitors can additionally be employed in all procedures leading to contact of the blood with foreign surfaces such as, for example, for dialysis patients and patients with indwelling catheters. TAFIa inhibitors can be employed to reduce the risk of thrombosis after surgical procedures such as knee and hip joint operations.

TAFIa inhibitors are suitable for the treatment of patients with disseminated intravascular coagulation, sepsis and other intravascular events associated with an inflammation. TAFIa inhibitors are additionally suitable for the prophylaxis and treatment of patients with atherosclerosis, diabetes and the metabolic syndrome and its sequelae. Impairments of the hemostatic system (e.g. fibrin deposits) have been implicated in mechanisms leading to tumor growth and tumor metastasis, and for inflammatory and degenerative articular disorders such as rheumatoid arthritis and arthrosis. TAFIa inhibitors are suitable for slowing down or preventing such processes.

Further indications for the use of TAFIa inhibitors are fibrotic changes of the lung such as chronic obstructive lung disease, adult respiratory distress syndrome (ARDS) and of the eye such as fibrin deposits after eye operations. TAFIa inhibitors are also suitable for the prevention and/or treatment of scar formation.

The medicaments of the invention can be administered by oral, inhalational, rectal or transdermal administration or by subcutaneous, intraarticular, intraperitoneal or intravenous injection. Oral administration is preferred. It is possible for stents and other surfaces which come into contact with blood in the body to be coated with TAFIa inhibitors.

The invention also relates to a process for producing a medicament, which comprises making a suitable dosage form from at least one compound of the formula I with a pharmaceutically suitable and physiologically tolerated carrier and, where appropriate, further suitable active ingredients, additives or excipients.

Suitable solid or pharmaceutical formulations are, for example, granules, powder, coated tablets, tablets, (micro) capsules, suppositories, syrups, solutions, suspensions, emulsions, drops or injectable solutions, and products with protracted release of active ingredient, in the production of which conventional aids such as carriers, disintegrants, binders, coating agents, swelling agents, glidants or lubricants, flavorings, sweeteners and solubilizers are used. Excipients which are frequently used and which may be mentioned are magnesium carbonate, titanium dioxide, lactose, mannitol and other sugars, talc, milk protein, gelatin, starch, cellulose and its derivatives, animal and vegetable oils such as fish liver oil, sunflower, peanut or sesame oil, polyethylene glycol and solvents such as, for example, sterile water and monohydric or polyhydric alcohols such as glycerol.

The pharmaceutical products are preferably produced and administered in dosage units, where each unit comprises as active ingredient a particular dose of the compound of the invention of the formula I. In the case of solid dosage units such as tablets, capsules, coated tablets or suppositories, this dose can be up to about 1000 mg, but preferably about 50 to 300 mg and, in the case of injection solutions in ampoule form, up to about 300 mg but preferably about 10 to 100 mg.

The daily doses indicated for the treatment of an adult patient weighing about 70 kg are, depending on the activity of the compound of formula I, from about 2 mg to 1000 mg of active ingredient, preferably about 50 mg to 500 mg. However, in some circumstances, higher or lower daily doses may also be appropriate. The daily dose can be administered either by a single administration in the form of a single dosage unit or else a plurality of smaller dosage units or by multiple administration of divided doses at particular intervals.

TAFIa inhibitors can be administered both as monotherapy and in combination or together with all antithrombotics (anticoagulants and platelet aggregation inhibitors), thrombolytics (plasminogen activators of every type), other substances having profibrinolytic activity, antihypertensives, regulators of blood glucose, lipid-lowering agents and antiarrhythmics.

EXAMPLES

Final products are normally determined by mass spectroscopic methods (FAB-, ESI-MS) and $^1$H-NMR; the main peak or two main peaks are indicated in each case. Temperatures are stated in degrees Celsius, RT means room temperature (21° C. to 24° C.). Abbreviations used are either explained or correspond to usual conventions. Unless stated otherwise, the LC/MS analyses were carried out under the following conditions:
Method A: column: YMC Jsphere 33×2.1 mm, packing 4 μm, mobile phase: $CH_3CN$+0.05% trifluoroacetic acid (TFA): $H_2O$+0.05% TFA, gradient: 5:95 (0 min) to 95:5 (2.5 min) to 95:5 (3.0 min), flow rate: 1.3 ml/min, temperature: 30° C.
Method B: column: YMC Jsphere 33×2.1 mm, packing 4 μm, mobile phase: $CH_3CN$+0.05% TFA: $H_2O$+0.05% TFA, gradient: 5:95 (0 min) to 95:5 (3.4 min) to (4.4 min), flow rate: 1 ml/min, temperature: 30° C.

Unless indicated otherwise, chromatographic separations were carried out on silica gel with ethyl acetate/heptane mixtures as mobile phase. Preparative separations on reversed phase (RP) silica gel (HPLC) were, unless indicated otherwise, carried out under the following conditions: column Merck Hibar RT 250-25 LiChrospher 100 RP-18e 5 μm, mobile phase A: $H_2O$+0.1% TFA, phase B: 80% acetonitrile+0.1% TFA, flow rate 25 ml/min, 0-7 min 100% A, 7-22 min to 100% B, 22-30 min 100% B, 30-33 min to 100% A, 33-35 min 100% A.

Evaporation of solvents normally took place under reduced pressure in a rotary evaporator at 35° C. to 45° C.

Example 1

3-(6-Aminopyridin-3-yl)-2-{1-[5-(5-chlorothiophen-2-yl)isoxazol-3-ylmethyl]-1H-imidazol-4-yl}propionic acid a) Methyl 3-(6-aminopyridin-3-yl)-2-{1-[5-(5-chlorothiophen-2-yl)isoxazol-3-ylmethyl]-1H-imidazol-4-yl}propionate trifluoroacetate Under argon, 0.032 g (1.340 mmol) of sodium hydride was added to a solution of 0.300 g (1.218 mmol) of methyl 3-(6- aminopyridin-3-yl)-2-(1H-imidazol-4-yl)propionate in 5 ml of absolute dimethylformamide (DMF), and the mixture was stirred at RT for 30 min. 0.339 g (1.218 mmol) of 3-bromomethyl-5-(5-chlorothiophen-2-yl)isoxazole was then added, and the reaction mixture was stirred at RT for a further 3 h and then concentrated. The residue was purified by preparative HPLC. Freeze-dying of the fraction of value gave the title compound as the trifluoroacetic acid salt. Yield 0.450 g (66%).

LC/MS: $R_t$=1.17 min, [M+H]$^+$=444 (method A).

b) 3-(6-Aminopyridin-3-yl)-2-{1-[5-(5-chlorothiophen-2-yl)isoxazol-3-ylmethyl]-1H-imidazol-4-yl}propionic acid A solution comprising 0.45 g (0.81 mmol) of methyl 3-(6-aminopyridin-3-yl)-2-{1-[5-(5-chlorothiophen-2-yl)isoxazol-3-ylmethyl]-1H-imidazol-4-yl}propionate in 10 ml of semi-concentrated hydrochloric acid was stirred at 90° C. for 1 h. After cooling, the mixture was concentrated and the crude product was purified by preparative HPLC. Freeze-dying of the fraction of value gave the title compound as the trifluoroacetic acid salt. Yield 0.35 g (80%).

LC/MS: $R_t$=1.17 min, [M+H]$^+$=430, chloro pattern (method A). $^1$H-NMR (DMSO-$d_6$, 500 MHz): δ [ppm]=13.75 (s, br, 1H), 8.81 (s, br, 1H), 8.00 (s, br, 2H), 7.72 (m, 2H), 7.61 (d, 1H), 7.50 (s, 1H), 7.32 (d, 1H), 6.93 (s, 1H), 6.88 (d, 1H), 5.51 (s, 1H), 4.05 (t, 1H), 3.14 (dd, 1H), 3.00 (dd, 1H).

Example 2

3-(6-Aminopyridin-3-yl)-2-[1-(5-phenylisoxazol-3-ylmethyl)-1H-imidazol-4-yl]propionic acid a) Methyl 3-(6-aminopyridin-3-yl)-2-[1-(5-phenylisoxazol-3-ylmethyl)-1H-imidazol-4-yl]propionate Under argon, 0.041 g (1.624 mmol) of sodium hydride was added to a solution of 0.400 g (1.624 mmol) of methyl 3-(6-aminopyridin-3-yl)-2-(1H-imidazol-4-yl)propionate in 15 ml of absolute DMF, and the mixture was stirred at RT for 30 min. 0.387 g (1.624 mmol) of 3-bromomethyl-5-phenylisoxazole was then added, and the reaction mixture was stirred at RT for a further 3 h and then concentrated. The residue was taken up in ethyl acetate, washed with water, dried over Na$_2$SO$_4$ and concentrated. The crude product was chromatographed on silica gel (mobile phase dichloromethane/methanol/acetic acid/water 90:10:1:1). Freeze-dying of the fraction of value gave the title compound as the acetate. Yield. 0.600 g (80%).

LC/MS: $R_t$=1.1 min, [M+H]$^+$=404 (method B).

b) 3-(6-Aminopyridin-3-yl)-2-[1-(5-phenylisoxazol-3-ylmethyl)-1H-imidazol-4-yl]propionic acid 6.1 ml (6.1 mmol) of a 1 M lithium hydroxide solution was added to a solution of 0.564 g (1.216 mmol) of the compound from Example 2a) in 45 ml of THF/methanol (2:1, v/v), and the mixture was heated at 50° C. for 2 h. The organic solvents were distilled off and the residue was purified by preparative HPLC. Freeze-dying of the fraction of value gave the title compound as the trifluoroacetic acid salt. Yield 0.314 g (51%).

LC/MS: $R_t$=1.08 min, [M+H]$^+$=390 (method A). $^1$H-NMR (DMSO-$d_6$, 500 MHz): δ [ppm]=13.7 (s, br, 1H), 8.89 (s, br, 1H), 8.03 (s, br, 2H), 7.87 (d, 2H), 7.72 (m, 2H), 7.55 (m, 4H), 7.03 (s, 1H), 6.88 (d, 1H), 5.53 (s, 2H), 4.09 (t, 1H), 3.17 (dd, 1H), 3.01 (dd, 1H).

Example 3

3-(6-Aminopyridin-3-yl)-2-{1-[2-(5-chlorothiophen-2-yl)thiazol-5-ylmethyl]-1H-imidazol-4-yl}propionic acid The title compound was obtained analogously to Example 2 as trifluoroacetic acid salt from 5-bromomethyl-2-(5-chlorothiophen-2-yl)thiazole.

LC/MS: $R_t$=1.03 min, [M+H]$^+$=446, chloro pattern (method A). $^1$H-NMR (DMSO-$d_6$, 500 MHz): δ [ppm]=13.8 (s, br, 1H), 8.65 (s, br, 1H), 8.02 (s, br, 2H), 7.98 (s, 1H), 7.72 (m, 2H), 7.58 (d, 1H), 7.45 (s, 1H), 7.21 (d, 1H), 6.85 (d, 1H), 5.61 (s, 2H), 4.03 (t, 1H), 3.12 (dd, 1H), 2.99 (dd, 1H).

Example 4

3-(6-Aminopyridin-3-yl)-2-[1-(6-chlorothieno[2,3-b]pyridin-2-ylmethyl)-1H-imidazol-4-yl]propionic acid The title compound was obtained analogously to Example 2 as trifluoroacetic acid salt from 2-bromomethyl-6-chlorothieno[2,3-b]pyridine.

LC/MS: $R_t$=0.85 min, [M+H]$^+$=414, chloro pattern (method A). $^1$H-NMR (DMSO-$d_6$, 500 MHz): δ [ppm]=13.8 (s, br, 1H), 8.65 (s, br, 1H), 8.32 (d, 1H), 7.94 (s, br, 2H), 7.68 (m, 2H), 7.56 (d, 1H), 7.46 (m, 2H), 6.83 (d, 1H), 5.65 (s, 2H), 4.02 (t, 1H), 3.12 (dd, 1H), 2.99 (dd, 1H).

Example 5

3-(6-Aminopyridin-3-yl)-2-{1-[5-(4-methoxyphenyl)isoxazol-3-ylmethyl]-1H-imidazol-4-yl}propionic acid The title compound was obtained analogously to Example 2 as trifluoroacetic acid salt from 3-bromomethyl-5-(4-methoxyphenyl)isoxazole.

LC/MS: $R_t$=1.04 min, [M+H]$^+$=420 (method A). $^1$H-NMR (DMSO-$d_6$, 500 MHz): δ [ppm]=13.8 (s, br, 1H), 8.91 (s, br, 1H), 8.03 (s, br, 2H), 7.78 (d, 2H), 7.72 (m, 2H), 7.57 (s, 1H), 7.08 (d, 2H), 6.91 (s, 1H), 6.88 (d, 1H), 5.52 (s, 2H), 4.12 (t, 1H), 3.85 (s, 3H), 3.18 (dd, 1H), 3.02 (dd, 1H).

Example 6

3-(6-Aminopyridin-3-yl)-2-{1-[5-(3-methylbutyl)isoxazol-3-ylmethyl]-1H-imidazol-4-yl}propionic acid The title compound was obtained analogously to Example 2 as trifluoroacetic acid salt from 3-bromomethyl-5-(3-methylbutyl)isoxazole.

LC/MS: $R_t$=1.11 min, [M+H]$^+$ 384=(method A). $^1$H-NMR (DMSO-$d_6$, 500 MHz): δ [ppm]=13.7 (s, br, 1H), 8.82 (s, br, 1H), 8.02 (s, br, 2H), 7.72 (m, 2H), 7.49 (s, 1H), 6.87 (d, 1H), 6.30 (s, 1H), 5.45 (s, 2H), 4.08 (t, 1H), 3.16 (dd, 1H), 3.02 (dd, 1H), 2.76 (t, 2H), 1.59-1.48 (m, 3H), 0.88 (d, 6H).

Example 7

3-(6-Aminopyridin-3-yl)-2-{1-[5-(5-chlorothiophen-2-yl)-[1,3,4]thiadiazol-2-ylmethyl]-1H-imidazol-4-yl}propionic acid The title compound was obtained analogously to Example 2 as trifluoroacetic acid salt from 2-bromomethyl-5-(5-chlorothiophen-2-yl)-[1,3,4]thiadiazole.

LC/MS: $R_t$=1.09 min, $[M+H]^+$=447, chloro pattern (method A). $^1$H-NMR (DMSO-$d_6$, 500 MHz): δ [ppm]=13.8 (s, br, 1H), 8.68 (s, br, 1H), 7.98 (s, br, 2H), 7.73 (m, 3H), 7.47 (s, 1H), 7.32 (d, 1H), 6.87 (d, 1H), 5.87 (s, 2H), 4.05 (t, 1H), 3.13 (dd, 1H), 3.02 (dd, 1H).

Example 8

3-(6-Aminopyridin-3-yl)-2-{1-[5-(4-chlorophenyl)-[1,3,4]thiadiazol-2-ylmethyl]-1H-imidazol-4-yl}propionic acid The title compound was obtained analogously to Example 2 as trifluoroacetic acid salt from 2-chloromethyl-5-(4-chlorophenyl)-[1,3,4]thiadiazole.

LC/MS: $R_t$=1.13 min, $[M+H]^+$=441, chloro pattern (method A). $^1$H-NMR (DMSO-$d_6$, 500 MHz): δ [ppm]=13.8 (s, br, 1H), 8.70 (s, br, 1H), 7.98 (m, 4H), 7.71 (d, 2H), 7.62 (d, 2H), 7.52 (s, 1H), 6.88 (d, 1H), 5.90 (s, 2H), 4.03 (t, 1H), 3.15 (dd, 1H), 3.02 (dd, 1H).

Example 9

3-(6-Aminopyridin-3-yl)-2-[1-(5-tert-butyl-[1,3,4]thiadiazol-2-ylmethyl)-1H-imidazol-4-yl]propionic acid The title compound was obtained analogously to Example 2 as trifluoroacetic acid salt from 2-tert-butyl-5-chloromethyl-[1,3,4]thiadiazole.

LC/MS: $R_t$=0.89 min, $[M+H]^+$=387 (method A). $^1$H-NMR (DMSO-$d_6$, 500 MHz): δ [ppm]=13.6 (s, br, 1H), 8.55 (s, br, 1H), 8.01 (s, br, 2H), 7.72 (m, 2H), 7.46 (s, 1H), 6.86 (d, 1H), 5.79 (s, 2H), 4.03 (t, 1H), 3.12 (dd, 1H), 3.00 (dd, 1H), 1.42 (s, 9H).

Example 10

3-(6-Aminopyridin-3-yl)-2-{1-[5-(4-trifluoromethylphenyl)-[1,2,4]oxadiazol-3-ylmethyl]-1H-imidazol-4-yl}propionic acid The title compound was obtained analogously to Example 2 as trifluoroacetic acid salt from 3-chloromethyl-5-(4-trifluoromethylphenyl)-[1,2,4]oxadiazole.

LC/MS: $R_t$=1.12 min, $[M+H]^+$=459 (method A). $^1$H-NMR (DMSO-$d_6$, 500 MHz): δ [ppm]=13.8 (s, br, 1H), 8.72 (s, br, 1H), 8.30 (d, 2H), 8.05 (d, 2H), 8.03 (s, 2H), 7.73 (m, 2H), 7.52 (s, 1H), 6.87 (d, 1H), 5.72 (s, 2H), 4.08 (t, 1H), 3.15 (dd, 1H), 3.02 (dd, 1H).

Example 11

3-(6-Aminopyridin-3-yl)-2-{1-[5-(3-trifluoromethylphenyl)-[1,2,4]oxadiazol-3-ylmethyl]-1H-imidazol-4-yl}propionic acid The title compound was obtained analogously to Example 2 as trifluoroacetic acid salt from 3-chloromethyl-5-(3-trifluoromethylphenyl)-[1,2,4]oxadiazole.

LC/MS: $R_t$=1.07 min, $[M+H]^+$=459 (method A). $^1$H-NMR (DMSO-$d_6$, 500 MHz): δ [ppm]=13.9 (s, br, 1H), 8.79 (s, br, 1H), 8.40 (d, 1H), 8.35 (s, 1H), 8.12 (d, 1H), 8.02 (s, br, 2H), 7.92 (t, 1H), 7.73 (m, 2H), 7.55 (s, 1H), 6.88 (d, 1H), 5.73 (s, 2H), 4.10 (t, 1H), 3.17 (dd, 1H), 3.04 (dd, 1H).

Example 12

3-(6-Aminopyridin-3-yl)-2-[1-(5-cyclopropyl-[1,3,4]thiadiazol-2-ylmethyl)-1H-imidazol-4-yl]propionic acid The title compound was obtained analogously to Example 2 as trifluoroacetic acid salt from 2-chloromethyl-5-cyclopropyl-[1,3,4]-thiadiazole.

LC/MS: $R_t$=0.62 min, $[M+H]^+$=371 (method A). $^1$H-NMR (DMSO-$d_6$, 500 MHz): δ [ppm]=13.8 (s, br, 1H), 8.59 (s, br, 1H), 8.00 (s, br, 2H), 7.72 (m, 2H), 7.40 (s, 1H), 6.88 (d, 1H), 5.75 (s, 2H), 4.03 (t, 1H), 3.11 (dd, 1H), 3.00 (dd, 1H), 2.55 (m, 1H), 1.21 (m, 2H), 0.99 (m, 2H).

Example 13

3-(6-Aminopyridin-3-yl)-2-[1-(5-phenyl-[1,2,4]oxadiazol-3-ylmethyl)-1H-imidazol-4-yl]propionic acid The title compound was obtained analogously to Example 2 as trifluoroacetic acid salt from 3-chloromethyl-5-phenyl-[1,2,4]oxadiazole.

LC/MS: $R_t$=0.87 min, $[M+H]^+$=391 (method A). $^1$H-NMR (DMSO-$d_6$, 500 MHz): δ [ppm]=13.7 (s, br, 1H), 8.76 (s, br, 1H), 8.10 (d, 2H), 8.06 (s, 2H), 7.73 (m, 3H), 7.68 (t, 2H), 7.52 (s, 1H), 6.89 (d, 1H), 5.70 (s, 2H), 4.10 (t, 1H), 3.16 (dd, 1H), 3.03 (dd, 1H).

Example 14

3-(6-Aminopyridin-3-yl)-2-{1-[3-(3,4-dimethoxyphenyl)-[1,2,4]oxadiazol-5-ylmethyl]-1H-imidazol-4-yl}propionic acid The title compound was obtained analogously to Example 2 as trifluoroacetic acid salt from 5-chloromethyl-3-(3,4-dimethoxyphenyl)-[1,2,4]oxadiazole.

LC/MS: $R_t$=0.89 min, $[M+H]^+$=451 (method A). $^1$H-NMR (DMSO-$d_6$, 500 MHz): δ [ppm]=13.5 (s, br, 1H), 8.62 (s, br, 1H), 7.99 (s, br, 2H), 7.71 (m, 2H), 7.53 (m, 2H), 7.42 (s, 1H), 7.12 (d, 1H), 6.88 (d, 1H), 5.85 (s, 2H), 4.08 (t, 1H), 3.72, (s, 3H), 3.71 (s, 3H), 3.15 (dd, 1H), 3.03 (dd, 1H).

Example 15

3-(6-Aminopyridin-3-yl)-2-{1-[3-(4-methoxyphenyl)-[1,2,4]oxadiazol-5-ylmethyl]-1H-imidazol-4-yl}propionic acid The title compound was obtained analogously to Example 2 as trifluoroacetic acid salt from 3-chloromethyl-5-(4-methoxyphenyl)-[1,2,4]oxadiazole.

LC/MS: $R_t$=0.96 min, [M+H]$^+$=421 (method A). $^1$H-NMR (DMSO-d$_6$, 500 MHz): δ [ppm]=13.7 (s, br, 1H), 8.69 (s, br, 1H), 8.03 (m, 4H), 7.73 (m, 2H), 7.50 (s, 1H), 7.18 (d, 2H), 6.88 (d, 1H), 5.62 (s, 2H), 4.08 (t, 1H), 3.89 (s, 3H), 3.15 (dd, 1H), 3.01 (dd, 1H).

Example 16

3-(6-Aminopyridin-3-yl)-2-{1-[3-(4'-isopropylphenyl)-[1,2,4]oxadiazol-5-ylmethyl]-1H-imidazol-4-yl}propionic acid The title compound was obtained analogously to Example 2 as trifluoroacetic acid salt from 5-chloromethyl-3-(4-isopropylphenyl)-[1,2,4]oxadiazole.

LC/MS: $R_t$=1.19 min, [M+H]$^+$=433 (method A). $^1$H-NMR (DMSO-d$_6$, 500 MHz): δ [ppm]=13.5 (s, br, 1H), 8.53 (s, br, 1H), 8.02 (s, br, 2H), 7.90 (d, 2H), 7.75 (m, 2H), 7.50 (s, 1H), 7.46 (d, 2H), 6.88 (d, 1H), 5.87 (s, 2H), 4.06 (t, 1H), 3.15 (dd, 1H), 3.04-2.92 (m, 2H), 1.22 (d, 6H).

Example 17

3-(6-Aminopyridin-3-yl)-2-{1-[3-(4'-tert-butylphenyl)-[1,2,4]oxadiazol-5-ylmethyl]-1H-imidazol-4-yl}propionic acid The title compound was obtained analogously to Example 2 as trifluoroacetic acid salt from 5-chloromethyl-3-(4-tert-butylphenyl)-[1,2,4]oxadiazole.

LC/MS: $R_t$=1.26 min, [M+H]$^+$=447 (method A). $^1$H-NMR (DMSO-d$_6$, 500 MHz): δ [ppm]=13.6 (s, br, 1H), 8.52 (s, br, 1H), 8.00 (s, br, 2H), 7.90 (d, 2H), 7.75 (m, 2H), 7.61 (d, 2H), 7.50 (s, 1H), 6.89 (d, 1H), 5.88 (s, 2H), 4.05 (t, 1H), 3.15 (dd, 1H), 3.03 (dd, 1H), 1.32 (s, 9H).

Example 18

3-(6-Aminopyridin-3-yl)-2-{1-[5-(2-methylthiazol-4-yl)isoxazol-3-ylmethyl]-1H-imidazol-4-yl}propionic acid The title compound was obtained analogously to Example 2 as trifluoroacetic acid salt from 3-bromomethyl-5-(2-methylthiazol-4-yl)isoxazole.

LC/MS: $R_t$=0.77 min, [M+H]$^+$=411 (method A), $^1$H-NMR (DMSO-d$_6$, 500 MHz): δ [ppm]=13.7 (s, br, 1H), 8.88 (s, br, 1H), 8.20 (s, 1H), 8.03 (s, br, 2H), 7.72 (m, 2H), 7.54 (s, 1H), 6.92 (s, 1H), 6.89 (d, 1H), 5.55 (s, 2H), 4.10 (t, 1H), 3.17 (dd, 1H), 3.02 (dd, 1H), 2.72 (s, 3H).

Example 19

3-(6-Aminopyridin-3-yl)-2-{1-[5-(3,4-dichlorophenyl)isoxazol-3-ylmethyl]-1H-imidazol-4-yl}propionic acid The title compound was obtained analogously to Example 2 as trifluoroacetic acid salt from 3-bromomethyl-5-(3,4-dichlorophenyl)isoxazole.

LC/MS: $R_t$=1.18 min, [M+H]$^+$=458, dichloro pattern (method A). $^1$H-NMR (DMSO-d$_6$, 500 MHz): δ [ppm]=13.8 (s, br, 1H), 8.83 (s, br, 1H), 8.18 (s, 1H), 8.01 (s, br, 2H), 7.86 (m, 2H), 7.72 (m, 2H), 7.54 (s, 1H), 7.87 (d, 1H), 5.58 (s, 2H), 4.10 (t, 1H), 3.17 (dd, 1H), 3.02 (dd, 1H).

Example 20

3-(6-Aminopyridin-3-yl)-2-{1-[3-(4-methoxyphenyl)-[1,2,4]oxadiazol-5-ylmethyl]-1H-imidazol-4-yl}propionic acid The title compound was obtained analogously to Example 2 as trifluoroacetic acid salt from 5-chloromethyl-3-(4-methoxyphenyl)-[1,2,4]oxadiazole.

LC/MS: $R_t$=0.90 min, [M+H]$^+$=421 (method A). $^1$H-NMR (DMSO-d$_6$, 500 MHz): δ [ppm]=13.5 (s, br, 1H), 8.56 (s, br, 1H), 8.01 (s, br, 2H), 7.91 (d, 2H), 7.76 (m, 2H), 7.49 (s, 1H), 7.11 (d, 2H), 6.88 (d, 1H), 5.82 (s, 2H), 4.07 (t, 1H), 3.82 (s, 3H), 3.15 (dd, 1H), 3.03 (dd, 1H).

Example 21

3-(6-Aminopyridin-3-yl)-2-[1-(5-phenyl-[1,3,4]thiadiazol-2-ylmethyl)-1H-imidazol-4-yl]propionic acid The title compound was obtained analogously to Example 2 as trifluoroacetic acid salt from 2-bromomethyl-5-phenyl-[1,3,4]thiadiazole.

LC/MS: $R_t$=0.81 min, [M+H]$^+$=407 (method A). $^1$H-NMR (DMSO-d$_6$, 500 MHz): δ [ppm]=13.8 (s, br, 1H), 8.78 (s, br, 1H), 8.03 (s, br, 2H), 7.98 (d, 2H), 7.73 (m, 2H), 7.58 (m, 4H), 6.88 (d, 1H), 5.91 (s, 2H), 4.09 (t, 1H), 3.15 (dd, 1H), 3.03 (dd, 1H).

Example 22

3-(6-Aminopyridin-3-yl)-2-{1-[5-(4-methoxyphenyl)-[1,3,4]thiadiazol-2-ylmethyl]-1H-imidazol-4-yl}propionic acid The title compound was obtained analogously to Example 2 as trifluoroacetic acid salt from 2-bromomethyl-5-(4-methoxyphenyl)-[1,3,4]thiadiazole.

LC/MS: $R_t$=0.87 min, [M+H]$^+$=437 (method A). $^1$H-NMR (DMSO-d$_6$, 500 MHz): δ [ppm]=13.8 (s, br, 1H), 8.77 (s, br, 1H), 8.02 (s, br, 2H), 7.91 (d, 2H), 7.72 (m, 2H), 7.52 (s, 1H), 7.11 (d, 2H), 6.88 (d, 1H), 5.88 (s, 2H), 4.08 (t, 1H), 3.85 (s, 3H), 3.15 (dd, 1H), 3.02 (dd, 1H).

Example 23

3-(6-Aminopyridin-3-yl)-2-{1-[5-(3,5-dimethylisoxazol-4-yl)-[1,2,4]oxadiazol-3-ylmethyl]-1H-imidazol-4-yl}propionic acid The title compound was obtained analogously to Example 2 as trifluoroacetic acid salt from 3-chloromethyl-5-(3,5-dimethylisoxazol-4-yl)-[1,2,4]oxadiazole.

LC/MS: $R_t$=0.72 min, [M+H]$^+$=410 (method A). $^1$H-NMR (DMSO-d$_6$, 500 MHz): δ [ppm]=13.6 (s, br, 1H), 8.60 (s, br, 1H), 7.98 (s, br, 2H), 7.73 (m, 2H), 7.44 (s, 1H), 6.86 (d, 1H), 5.65 (s, 2H), 4.07 (t, 1H), 3.13 (dd, 1H), 3.03 (dd, 1H), 2.72 (s, 3H), 2.48 (s, 3H).

Example 24

3-(6-Aminopyridin-3-yl)-2-[1-(5-thiophen-2-ylisoxazol-3-ylmethyl)-1H-imidazol-4-yl]propionic acid The title compound was obtained analogously to Example 2 as trifluoroacetic acid salt from 3-bromomethyl-5-thiophen-2-isoxazole.

LC/MS: $R_t$=0.86 min, [M+H]$^+$=396 (method B). $^1$H-NMR (DMSO-d$_6$, 500 MHz): δ [ppm]=13.9 (s, br, 1H), 8.90 (s, br, 1H), 8.02 (s, br, 2H), 8.86 (d, 1H), 7.70 (m, 3H), 7.58 (s, 1H), 7.25 (dd, 1H), 6.89 (m, 2H), 5.53 (s, 2H), 4.10 (t, 1H), 3.16 (dd, 1H), 3.02 (dd, 1H).

Example 25

3-(6-Aminopyridin-3-yl)-2-[1-(5-tert-butyl-1,2,4-oxadiazol-3-ylmethyl)-1H-imidazol-4-yl]propionic acid The title compound was obtained analogously to Example 2 as trifluoroacetic acid salt from 5-(tert-butyl)-3-(chloromethyl)-1,2,4-oxadiazole.

LC/MS: $R_t$=0.77 min, $[M+H]^+$=371 (method B). $^1$H-NMR (DMSO-$d_6$, 500 MHz): δ [ppm]=13.7 (s, br, 1H), 8.80 (s, br, 1H), 8.06 (s, br, 2H), 7.72 (m, 2H), 7.51 (s, 1H), 6.88 (d, 1H), 5.59 (s, 2H), 4.42 (t, 1H), 3.16 (dd, 1H), 3.01 (dd, 1H), 1.48 (s, 9H).

Example 26

3-(6-Aminopyridin-3-yl)-2-(1-{3-[4-(4-chlorobenzyloxy)phenyl]-[1,2,4]oxadiazol-5-ylmethyl}-1H-imidazol-4-yl)propionic acid The title compound was obtained analogously to Example 2 as trifluoroacetic acid salt from 3-[4-(4-chlorobenzyloxy)phenyl]-5-chloromethyl-[1,2,4]oxadiazole.

LC/MS: $R_t$=1.36 min, $[M+H]^+$=371, chloro pattern, (method A).

Example 27

3-(6-Aminopyridin-3-yl)-2-[1-(4-bromothiophen-2-ylmethyl)-1H-imidazol-4-yl]propionic acid The title compound was obtained analogously to Example 2 as trifluoroacetic acid salt from 4-bromothiophen-2-ylmethyl methanesulfonate.

LC/MS: $R_t$=0.80 min, $[M+H]^+$=407, bromo pattern (method A).

Example 28

3-(6-Aminopyridin-3-yl)-2-[1-(5-methylisoxazol-3-ylmethyl)-1H-imidazol-4-yl]propionic acid The title compound was obtained analogously to Example 2 as trifluoroacetic acid salt from 3-bromomethyl-5-methyl-isoxazole.

LC/MS: $R_t$=0.52 min, $[M+H]^+$=328 (method A).

Example 29

3-(6-Aminopyridin-3-yl)-2-[1-(4-phenyl-5-trifluoromethylthiophen-2-ylmethyl)-1H-imidazol-4-yl]propionic acid The title compound was obtained analogously to Example 2 as trifluoroacetic acid salt from 4-phenyl-5-trifluoromethylthiophen-2-ylmethyl methanesulfonate.

LC/MS: $R_t$=1.36 min, $[M+H]^+$=473 (method A).

Example 30

3-(6-Aminopyridin-3-yl)-2-{1-[5-(4-bromophenyl)isoxazol-3-ylmethyl]-1H-imidazol-4-yl}propionic acid The title compound was obtained analogously to Example 2 as trifluoroacetic acid salt from 5-(4-bromophenyl)isoxazol-3-ylmethyl methanesulfonate.

LC/MS: $R_t$=1.11 min, $[M+H]^+$=468, bromo pattern (method A).

Example 31

3-(6-Aminopyridin-3-yl)-2-[1-(5-p-tolylisoxazol-3-ylmethyl)-1H-imidazol-4-yl]propionic acid The title compound was obtained analogously to Example 2 as trifluoroacetic acid salt from 5-(4-methylphenyl)isoxazol-3-ylmethyl methanesulfonate.

LC/MS: $R_t$=1.07 min, $[M+H]^+$=404 (method A).

Example 32

3-(6-Aminopyridin-3-yl)-2-(1-{2-[5-(5-chlorothiophen-2-yl)isoxazol-3-yl]-ethyl}-1H-imidazol-4-yl)propionic acid The title compound was obtained analogously to Example 2 as trifluoroacetic acid salt from 2-[5-(5-chlorothiophen-2-yl)isoxazol-3-yl]ethyl toluene-4-sulfonate.

LC/MS: $R_t$=1.05 min, $[M+H]^+$=444, chloro pattern (method A).

Example 33

3-(6-Aminopyridin-3-yl)-2-{1-[5-(4-isobutylphenyl)isoxazol-3-ylmethyl]-1H-imidazol-4-yl}propionic acid The title compound was obtained analogously to Example 2 as trifluoroacetic acid salt from 5-(4-isobutylphenyl)isoxazol-3-ylmethyl methanesulfonate.

LC/MS: $R_t$=1.29 min, $[M+H]^+$=446 (method A).

Example 34

3-(6-Aminopyridin-3-yl)-2-[1-(5-cyclopentyl-[1,3,4]thiadiazol-2-ylmethyl)-1H-imidazol-4-yl]propionic acid The title compound was obtained analogously to Example 2 as trifluoroacetic acid salt from 5-cyclopentyl-[1,3,4]thiadiazol-2-ylmethyl methanesulfonate.

LC/MS: $R_t$=0.82 min, $[M+H]^+$=399 (method A).

Example 35

3-(6-Aminopyridin-3-yl)-2-[1-(5-cyclobutyl-[1,3,4]thiadiazol-2-ylmethyl)-1H-imidazol-4-yl]propionic acid The title compound was obtained analogously to Example 2 as trifluoroacetic acid salt from 5-cyclobutyl-[1,3,4]thiadiazol-2-ylmethyl methanesulfonate.

LC/MS: $R_t$=0.71 min, $[M+H]^+$=385 (method A).

Example 36

3-(6-Aminopyridin-3-yl)-2-[1-(5-cyclopropyl isoxazol-3-ylmethyl)-1H-imidazol-4-yl]propionic acid The title compound was obtained analogously to Example 2 as trifluoroacetic acid salt from 5-cyclopropylisoxazol-3-ylmethyl methanesulfonate.
LC/MS: $R_t$=0.69 min, $[M+H]^+$=354 (method A).

Example 37

3-(6-Aminopyridin-3-yl)-2-[1-(5-cyclohexylisoxazol-3-ylmethyl)-1H-imidazol-4-yl]propionic acid The title compound was obtained analogously to Example 2 as trifluoroacetic acid salt from 5-cyclohexylisoxazol-3-ylmethyl methanesulfonate.
LC/MS: $R_t$=1.07 min, $[M+H]^+$=396 (method A).

Example 38

3-(6-Aminopyridin-3-yl)-2-{1-[5-cyclohexyl-[1,3,4]thiadiazol-2-ylmethyl]-1H-imidazol-4-yl}propionic acid The title compound was obtained analogously to Example 2 as trifluoroacetic acid salt from 5-cyclohexyl-[1,3,4]thiadiazol-2-ylmethyl methanesulfonate.
LC/MS: $R_t$=0.90 min, $[M+H]^+$=413 (method A).

Example 39

3-(6-Aminopyridin-3-yl)-2-{1-[5-(3-methylbutyl)-[1,3,4]thiadiazol-2-ylmethyl]-1H-imidazol-4-yl}propionic acid The title compound was obtained analogously to Example 2 as trifluoroacetic acid salt from 5-(3-methylbutyl)-[1,3,4]thiadiazol-2-ylmethyl methanesulfonate.
LC/MS: $R_t$=0.92 min, $[M+H]^+$=401 (method A).

Example 40

3-(6-Aminopyridin-3-yl)-2-[1-(5-cyclobutylisoxazol-3-ylmethyl)-1H-imidazol-4-yl]propionic acid The title compound was obtained analogously to Example 2 as trifluoroacetic acid salt from 5-cyclobutyl isoxazol-3-ylmethyl methanesulfonate.
LC/MS: $R_t$=0.89 min, $[M+H]^+$=368 (method A).

Example 41

3-(6-Aminopyridin-3-yl)-2-{1-[5-(4-fluorophenyl)isoxazol-3-ylmethyl]-1H-imidazol-4-yl}propionic acid The title compound was obtained analogously to Example 2 as trifluoroacetic acid salt from 5-(4-fluorophenyl)isoxazol-3-ylmethyl methanesulfonate.
LC/MS: $R_t$=1.04 min, $[M+H]^+$=408 (method A).

Example 42

3-(6-Aminopyridin-3-yl)-2-{1-[5-(4-benzylphenyl)isoxazol-3-ylmethyl]-1H-imidazol-4-yl}propionic acid The title compound was obtained analogously to Example 2 as trifluoroacetic acid salt from 5-(4-benzylphenyl)isoxazol-3-ylmethyl methanesulfonate.
LC/MS: $R_t$=1.28 min, $[M+H]^+$=480 (method A).

Example 43

3-(6-Aminopyridin-3-yl)-2-{1-[5-(4-tert-butylphenyl)isoxazol-3-ylmethyl]-1H-imidazol-4-yl}propionic acid The title compound was obtained analogously to Example 2 as trifluoroacetic acid salt from 5-(4-tert-butylphenyl)isoxazol-3-ylmethyl methanesulfonate.
LC/MS: $R_t$=1.28 min, $[M+H]^+$=446 (method A).

Example 44

3-(6-Aminopyridin-3-yl)-2-{1-[5-(4-tert-butyl-2,6-dimethylphenyl)isoxazol-3-ylmethyl]-1H-imidazol-4-yl}propionic acid The title compound was obtained analogously to Example 2 as trifluoroacetic acid salt from 5-(4-tert-butyl-2,6-dimethylphenyl)isoxazol-3-ylmethyl methanesulfonate.
LC/MS: $R_t$=1.34 min, $[M+H]^+$=474 (method A).

Example 45

3-(6-Aminopyridin-3-yl)-2-{1-[5-(2-chlorophenyl)isoxazol-3-ylmethyl]-1H-imidazol-4-yl}propionic acid The title compound was obtained analogously to Example 2 as trifluoroacetic acid salt from 5-(2-chlorophenyl)isoxazol-3-ylmethyl methanesulfonate.
LC/MS: $R_t$=1.05 min, $[M+H]^+$=424, chloro pattern (method A).

Example 46

3-(6-Aminopyridin-3-yl)-2-{1-[5-(4-sec-butylphenyl)isoxazol-3-ylmethyl]-1H-imidazol-4-yl}propionic acid The title compound was obtained analogously to Example 2 as trifluoroacetic acid salt from 5-(4-sec-butylphenyl)isoxazol-3-ylmethyl methanesulfonate.
LC/MS: $R_t$=1.29 min, $[M+H]^+$=446 (method A).

Example 47

3-(6-Aminopyridin-3-yl)-2-[1-(5-indan-5-ylisoxazol-3-ylmethyl)-1H-imidazol-4-yl]propionic acid The title compound was obtained analogously to Example 2 as trifluoroacetic acid salt from 5-indan-5-ylisoxazol-3-ylmethyl methanesulfonate.
LC/MS: $R_t$=1.15 min, $[M+H]^+$=430 (method A).

Example 48

3-(6-Aminopyridin-3-yl)-2-{1-[5-(4-cyclopentyl phenyl)isoxazol-3-ylmethyl]-1H-imidazol-4-yl}propionic acid The title compound was obtained analogously to Example 2 as trifluoroacetic acid salt from 5-(4-cyclopentylphenyl) isoxazol-3-ylmethyl methanesulfonate.
LC/MS: $R_t$=1.30 min, [M+H]$^+$=458 (method A).

Example 49

3-(6-Aminopyridin-3-yl)-2-{1-[5-(4-isopropylphenyl)isoxazol-3-ylmethyl]-1H-imidazol-4-yl}propionic acid The title compound was obtained analogously to Example 2 as trifluoroacetic acid salt from 5-(4-isopropylphenyl)isoxazol-3-ylmethyl methanesulfonate.
LC/MS: $R_t$=1.21 min, [M+H]$^+$=432 (method A).

Example 50

3-(6-Aminopyridin-3-yl)-2-{1-[5-(4-butylphenyl) isoxazol-3-ylmethyl]-1H-imidazol-4-yl}propionic acid The title compound was obtained analogously to Example 2 as trifluoroacetic acid salt from 5-(4-butylphenyl)isoxazol-3-ylmethyl methanesulfonate.
LC/MS: $R_t$=1.30 min, [M+H]$^+$=446 (method A).

Example 51

3-(6-Aminopyridin-3-yl)-2-{1-[5-(4-cyclohexylphenyl)isoxazol-3-ylmethyl]-1H-imidazol-4-yl}propionic acid The title compound was obtained analogously to Example 2 as trifluoroacetic acid salt from 5-(4-cyclohexylphenyl) isoxazol-3-ylmethyl methanesulfonate.
LC/MS: $R_t$=1.38 min, [M+H]$^+$=472 (method A).

Example 52

3-(6-Aminopyridin-3-yl)-2-{1-[5-(5,6,7,8-tetrahydronaphthalen-2-yl)isoxazol-3-ylmethyl]-1H-imidazol-4-yl}propionic acid The title compound was obtained analogously to Example 2 as trifluoroacetic acid salt from 5-(5,6,7,8-tetrahydronaphthalen-2-yl)isoxazol-3-ylmethyl methanesulfonate.
LC/MS: $R_t$=1.23 min, [M+H]$^+$=444 (method A).

Example 53

3-(6-Aminopyridin-3-yl)-2-{1-[5-(4-propylphenyl) isoxazol-3-ylmethyl]-1H-imidazol-4-yl}propionic acid The title compound was obtained analogously to Example 2 as trifluoroacetic acid salt from 5-(4-propylphenyl)isoxazol-3-ylmethyl methanesulfonate.
LC/MS: $R_t$=1.32 min, [M+H]$^+$=432 (method A).

Example 54

3-(6-Aminopyridin-3-yl)-2-{1-[5-(4-phenethylphenyl)isoxazol-3-ylmethyl]-1H-imidazol-4-yl}propionic acid The title compound was obtained analogously to Example 2 as trifluoroacetic acid salt from 5-(4-phenethylphenyl)isoxazol-3-ylmethyl methanesulfonate.
LC/MS: $R_t$=1.37 min, [M+H]$^+$=494 (method B).

Example 55

3-(6-Aminopyridin-3-yl)-2-{1-[5-(2,3-dihydrobenzo[1,4]dioxin-6-yl)isoxazol-3-ylmethyl]-1H-imidazol-4-yl}propionic acid The title compound was obtained analogously to Example 2 as trifluoroacetic acid salt from 5-(2,3-dihydrobenzo[1,4]dioxin-6-yl)isoxazol-3-ylmethyl methanesulfonate.
LC/MS: $R_t$=0.87 min, [M+H]$^+$=448 (method A).

Example 56

Ethyl (S)-3-(6-aminopyridin-3-yl)-2-{1-[5-(5-chlorothiophen-2-yl)isoxazol-3-ylmethyl]-1H-imidazol-4-yl}propionate Under argon, 0.485 g (60% in mineral oil, 19.21 mmol) of sodium hydride was added to a solution of 5.0 g (19.21 mmol) of 3-(6-aminopyridin-3-yl)-2-(1H-imidazol-4-yl)propionic acid in 200 ml of absolute DMF. The mixture was stirred for 30 min at RT, 5.643 g (19.21 mmol) of 5-(5-chlorothiophen-2-yl)isoxazol-3-ylmethyl methanesulfonate were then added and the mixture was stirred at RT for another 3 h. The reaction mixture was concentrated under reduced pressure, and the residue obtained was chromatographed on silica gel using CH$_2$Cl$_2$/MeOH/water/acetic acid 90:10:1:1. This gave two product-containing fractions which were purified by preparative HPLC. The fractions of value were combined and freeze-dried. The residue obtained was dissolved in ethyl acetate, washed with saturated NaHCO$_3$ solution, dried over Na$_2$SO$_4$, filtered and concentrated. The material obtained in this manner (3.7 g) was separated into its enantiomers by chiral HPLC (column Chiralpak AD-H/55, 250×4.6 mm, flow rate 1 ml/min, mobile phase heptane:isopropanol:methanol 3:1:1+ 0.1% TFA). 0.1 g (218 μmol) of the product obtained was dissolved in 5 ml of water/acetic acid (1:1) and freeze-dried (0.108 g, 95%).
LC/MS: $R_t$=1.14 min, [M+H]$^+$=458, chloro pattern (method A).
Chiral HPLC: $R_t$=5.312 min.

Example 57

Ethyl (R)-3-(6-aminopyridin-3-yl)-2-{1-[5-(5-chlorothiophen-2-yl)isoxazol-3-ylmethyl]-1H-imidazol-4-yl}propionate The title compound is obtained as second enantiomer in the preparation of Example 56.
LC/MS: $R_t$=1.14 min, [M+H]$^+$=458, chloro pattern (method A).
Chiral HPLC: $R_t$=8.443 min.

Example 58

(S)-3-(6-Aminopyridin-3-yl)-2-{1-[5-(5-chlorothiophen-2-yl)isoxazol-3-ylmethyl]-1H-imidazol-4-yl}propionic acid A solution of 0.11 g (0.24 mmol) of ethyl (S)-3-(6-aminopyridin-3-yl)-2-{1-[5-(5-chlorothiophen-2-yl)isoxazol-3-ylmethyl]-1H-imidazol-4-yl}propionate in 2 ml of semi-concentrated hydrochloric acid was stirred at RT for 24 h. The reaction mixture was freeze-dried and purified by preparative HPLC. The fractions of value obtained were combined and freeze-dried with 2 equivalents (eq) of 1N HCl (1×) and with 1 eq of 1N HCl and water (1×). This gave 0.077 g (69%) of the title compound as the hydrochloride.

LC/MS: $R_t$=1.07 min, $[M+H]^+$=430, chloro pattern (method A).

Example 59

(R)-3-(6-Aminopyridin-3-yl)-2-{1-[5-(5-chlorothiophen-2-yl)isoxazol-3-ylmethyl]-1H-imidazol-4-yl}propionic acid The title compound was obtained analogously to Example 58 as the hydrochloride.

LC/MS: $R_t$=1.02 min, $[M+H]^+$=430, chloro pattern (method A).

Example 60

6-Amino-2-[1-(5-cyclopropyl-[1,3,4]thiadiazol-2-ylmethyl)-1H-imidazol-4-yl]-hexanoic acid a) Diethyl 2-[1-(toluene-4-sulfonyl)-1H-imidazol-4-yl]malonate A solution of 1.000 g (3.243 mmol) of ethyl [1-(toluene-4-sulfonyl)-1H-imidazol-4-yl]-acetate was dissolved in 20 ml of THF and cooled to 0° C. Over a period of 10 min, 3.567 ml of lithium bis(trimethylsilyl)amide (3.567 mmol, 1M in THF) were added dropwise. This mixture was stirred at 0° C. for 30 min, 350 µl (3.567 mmol) of ethyl cyanoformate were then added and the mixture was stirred at RT for another 2 h. The reaction mixture was quenched with saturated ammonium chloride solution and extracted with ethyl acetate. The organic phase was washed with water and saturated NaCl solution, dried over $Na_2SO_4$, filtered and concentrated. Chromatography on silica gel (heptane/ethyl acetate 1:1) gave the title compound (0.390 g, 32%).

LC/MS: $R_t$=1.74 min, $[M+H]^+$=381, (method A).

b) Diethyl 2-(4-tert-butoxycarbonylaminobutyl)-2-[1-(toluene-4-sulfonyl)-1H-imidazol-4-yl]malonate 13.7 g (42.0 mmol) of cesium carbonate and 3.24 g (11.56 mmol) of 4-(t-butyloxycarbonylamino)butyl bromide were added to a solution of 4.0 g (10.51 mmol) of diethyl 2-[1-(toluene-4-sulfonyl)-1H-imidazol-4-yl]malonate in 67 ml of DMF, and the mixture was stirred at 60° C. for 2 h. The reaction mixture was concentrated under reduced pressure, and the residue was taken up in ethyl acetate and washed with water. The organic phase was dried over $Na_2SO_4$, filtered and concentrated. Chromatography on silica gel (heptane/ethyl acetate 1:1) gave the title compound (4.21 g, 73%). LC/MS: $R_t$=2.08 min, $[M+H]^+$=552, (method A).

c) Diethyl 2-(4-tert-butoxycarbonylaminobutyl)-2-(1H-imidazol-4-yl)malonate 4.2 g (7.61 mmol) of diethyl 2-(4-tert-butoxycarbonylaminobutyl)-2-[1-(toluene-4-sulfonyl)-1H-imidazol-4-yl]malonate were dissolved in 190 ml of methanol and stirred with 4.66 g (30.45 mmol) of 1-hydroxybenzotriazole hydrate at RT for 1 h. The reaction mixture was concentrated under reduced pressure, and the residue was chromatographed on silica gel ($CH_2Cl_2$:MeOH 9:1). The product-containing fractions were concentrated and the oil obtained was dissolved in ethyl acetate and washed with saturated $NaHCO_3$ solution. The organic phase was dried over $Na_2SO_4$, filtered and concentrated. This gave 2.14 g (71%) of the title compound.

LC/MS: $R_t$=1.26 min, $[M+H]^+$=398, (method A).

d) Diethyl 2-(4-tert-butoxycarbonylaminobutyl)-2-[1-(5-cyclopropyl-[1,3,4]thiadiazol-2-ylmethyl)-1H-imidazol-4-yl]malonate Together with 1.97 g (6.04 mmol) of cesium carbonate and 0.29 g (1.66 mmol) of 2-chloromethyl-5-cyclopropyl-1,3,4-thiadiazole, a solution of 0.60 g (1.51 mmol) of diethyl 2-(4-tert-butoxycarbonylaminobutyl)-2-(1H-imidazol-4-yl)malonate in 12 ml of DMF was heated at 75° C. for 2 h. The reaction mixture was concentrated under reduced pressure, and the residue was taken up in ethyl acetate and washed with water. The organic phase was dried over $Na_2SO_4$, filtered and concentrated. Chromatographic purification of the residue on silica gel ($CH_2Cl_2$:MeOH:water:acetic acid 95:5:0.5:0.5) gave 0.145 g (18%) of the title compound.

LC/MS: $R_t$=1.40 min, $[M+H]^+$=536, (method A).

e) 6-Amino-2-[1-(5-cyclopropyl-[1,3,4]thiadiazol-2-ylmethyl)-1H-imidazol-4-yl]-hexanoic acid 0.140 g (261 µmol) of diethyl 2-(4-tert-butoxycarbonylaminobutyl)-2-[1-(5-cyclopropyl-[1,3,4]thiadiazol-2-ylmethyl)-1H-imidazol-4-yl]malonate was suspended in 10 ml of semi-concentrated hydrochloric acid, and the mixture was heated with stirring at 95° C. for 8 h. The reaction mixture was concentrated under reduced pressure and purified by preparative HPLC, and the product-containing fractions were freeze-dried and then taken up in 2.5 eq of 1N hydrochloric acid and freeze-dried and taken up in water and freeze-dried. The preparation was then purified once more by preparative HPLC, and the product-containing fractions were freeze-dried. This gave 35 mg (32%) of the title compound as trifluoroacetic acid salt.

LC/MS: $R_t$=0.34 min, $[M+H]^+$=336, (method A).

Example 61

3-(6-Amino-5-methylpyridin-3-yl)-2-[1-(5-cyclopropyl-[1,3,4]thiadiazol-2-ylmethyl)-1H-imidazol-4-yl]propionic acid The title compound was obtained analogously to Example 60.

LC/MS: $R_t$=0.50 min, $[M+H]^+$=385 (method B).

Example 62

3-(4-Aminocyclohexyl)-2-[1-(5-cyclopropyl-[1,3,4]thiadiazol-2-ylmethyl)-1H-imidazol-4-yl]propionic acid The title compound was obtained analogously to Example 60.

LC/MS: $R_t$=0.64 min, $[M+H]^+$=376 (method A).

Example 63

3-(4-Aminocyclohexyl)-2-[1-(5-cyclopropyl-[1,3,4]thiadiazol-2-ylmethyl)-1H-imidazol-4-yl]propionic acid The title compound was obtained analogously to Example 60.

LC/MS: $R_t$=0.71 min, [M+H]$^+$=376 (method A).

Pharmacological Examples

The prepared substances were tested for TAFIa inhibition using the Actichrome plasma TAFI activity kit from Americian Diagnostica (Pr. No. 874). This entailed adding 29 µl of assay buffer (20 mM Hepes, 150 mM NaCl, pH 7.4) and 10 µl of TAFIa (American Diagnostica Pr. No. 874TAFIA; 2.5/ml) to 1 µl of 5 mM DMSO solution of the substance and incubating in a 96 half-well microtiter plate at room temperature for 15 minutes. The enzymic reaction was started by adding 10 µl of TAFIa developer (prediluted 1:2 with water). The time course of the reaction was followed at 420 nm in a microtiter plate reader (SpectraMax plus 384; Molecular Devices) for 15 minutes. The IC$_{50}$ values were calculated from the averaged values (duplicate determination) of serial dilutions of the substance with the aid of the Software Grafit 4 (Erithacus Software, UK). Table 1 shows the results.

TABLE 1

| Compound of Example | TAFIa enzyme assay IC$_{50}$ [micro M] |
| --- | --- |
| 1 | 0.041 |
| 3 | 0.326 |
| 5 | 0.104 |
| 8 | 0.041 |
| 9 | 0.169 |
| 10 | 0.258 |
| 12 | 0.030 |
| 15 | 0.223 |
| 17 | 0.745 |
| 18 | 0.326 |
| 22 | 0.078 |
| 46 | 0.003 |
| 58 | 0.004 |
| 61 | 0.026 |

What is claimed is:

1. A compound of formula I:

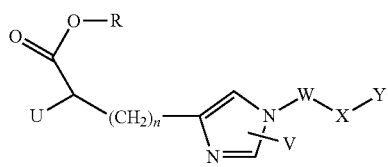

or any stereoisomeric fan of the compound of the formula I or a mixture of these forms in any ratio or a physiologically acceptable salt of the compound of the formula I where n is an integer zero or 1, U is: —(C$_1$-C$_4$)-alkylene-Het-Z in which Het is a heteroaromatic ring system having 4 to 15 carbon atoms which are present in one, two or three ring systems which are attached to one another and which contain one, two, three or four identical or different heteroatoms from the group consisting of oxygen, nitrogen and sulfur and in which Het is unsubstituted or mono-, di- or trisubstituted by —(C$_1$-C$_4$)-alkyl, or —(C$_0$-C$_2$)-alkylene-(C$_3$-C$_8$)-cycloalkyl-(C$_1$-C$_2$)—Z where Z is: a basic nitrogen-containing group, R is: a hydrogen atom; —(C$_1$-C$_6$)-alkyl; —(C$_1$-C$_6$)-alkylene-OH; —(C$_0$-C$_4$)-alkylene-(C$_3$-C$_6$)-cycloalkyl; —(C$_1$-C$_{10}$)-alkylene-O—C(O)—O—R1; —(C$_0$-C$_3$)-alkylene-(C$_6$-C$_{14}$)-aryl, where aryl is unsubstituted or independently of one another mono-, di- or trisubstituted by R1; or —(C$_0$-C$_3$)-alkylene-Het, where Het is as defined above and is unsubstituted or independently mono-, di- or trisubstituted by R1, V is: a hydrogen atom, —(C$_1$-C$_4$)-alkyl, halogen, —(C$_6$-C$_{14}$)-aryl, —NO$_2$, —NH$_2$, —OH or —CF$_3$, W is: —(C$_1$-C$_4$)-alkylene, where alkylene is unsubstituted or substituted by halogen, X is an aromatic five- to thirteen-membered heterocycle whose ring systems contain 5 to 13 carbon atoms which are present in one, two or three ring systems attached to one another and which may contain one, two, three or four identical or different heteroatoms from the group consisting of oxygen, nitrogen and sulfur, where the heterocycle is unsubstituted or mono-, di- or trisubstituted independently by R1, except for the case where X is pyridyl and Y is a hydrogen atom, Y is: —(C$_1$-C$_8$)-alkyl, where alkyl is unsubstituted or mono-, di- or trisubstituted independently by R1; —(C$_1$-C$_3$)-perfluoroalkyl; —(C$_0$-C$_4$)-alkylene-(C$_3$-C$_{12}$)-cycloalkyl, where cycloalkyl is unsubstituted or mono-, di- or trisubstituted independently by R1; —(C$_0$-C$_4$)-alkylene-(C$_6$-C$_{14}$)-aryl, where aryl is unsubstituted or mono-, di- or trisubstituted independently by R1; or —(C$_0$-C$_4$)-alkylene-heterocycle, where the heterocycle is an aromatic five- to thirteen-membered heterocycle whose ring systems contain 5 to 13 carbon atoms which are present in one, two or three ring systems attached to one another and which may contain one, two, three or four identical or different heteroatoms from the group consisting of oxygen, nitrogen and sulfur, where the heterocycle is unsubstituted or mono-, di- or trisubstituted independently by R1, if n is the integer zero, or Y is: —(C$_1$-C$_3$)-perfluoroalkyl; —(C$_0$-C$_4$)-alkylene-(C$_3$-C$_{12}$)-cycloalkyl, where cycloalkyl is unsubstituted or mono-, di- or trisubstituted independently by R1; —(C$_0$-C$_4$)-alkylene-(C$_6$-C$_{14}$)-aryl, where aryl is unsubstituted or mono-, di- or trisubstituted independently by R1; or —(C$_0$-C$_4$)-alkylene-heterocycle, where the heterocycle is as defined above and the heterocycle is unsubstituted or mono-, di- or trisubstituted independently by R1, if n is the integer 1, R1 is: a halogen; —NO$_2$; —CN; —N(R2)-R3, where R2 and R3 are identical or different and independently of one another are a hydrogen atom, —(C$_1$-C$_6$)-alkyl, —(C$_0$-C$_3$)-alkylene-(C$_6$-C$_{14}$)-aryl, —(C$_0$-C$_3$)-alkylene-Het, where Het is as defined above, or —(C$_0$-C$_3$)-alkylene-(C$_3$-C$_6$)-cycloalkyl; —OH; —C(O)—O—R4, where R4 is a hydrogen atom, —(C$_1$-C$_6$)-alkyl, —(C$_0$-C$_3$)-alkylene-(C$_6$-C$_{14}$)-aryl, —(C$_0$-C$_3$)-alkylene-Het, where Het is as defined above, or —(C$_0$-C$_3$)-alkylene-(C$_3$-C$_6$)-cycloalkyl; —C(O)—N(R2)-R3, where R2 and R3 are identical or different and independently of one another are as defined above; —O—CF$_3$; —(C$_0$-C$_4$)-alkylene-(C$_6$-C$_{14}$)-aryl, where aryl is unsubstituted or mono-, di- or trisubstituted independently by halogen, —(C$_1$-C$_4$)-alkyl, —(C$_3$-C$_8$)-cycloalkyl, halogen or —O—($C_1$-$C_8$)-alkyl; —($C_0$-$C_4$)-alkylene-($C_3$-$C_6$)-cycloalkyl; —($C_1$-$C_8$)-alkyl, where alkyl is unsubstituted or mono-, di- or trisubstituted independently by halogen, —$NH_2$, —OH or methoxy; —O—($C_1$-$C_8$)-alkyl, where alkyl is unsubstituted or mono-, di- or trisubstituted independently by halogen, —$NH_2$, —OH or methoxy; —O—($C_1$-$C_4$)-alkylene-($C_6$-$C_{14}$)-aryl, where aryl is unsubstituted or mono-, di- or trisubstituted independently by halogen, —($C_1$-$C_4$)-alkyl, —($C_3$-$C_8$)-cycloalkyl, or —O—($C_1$-$C_8$)-alkyl; —$SO_2$—$CH_3$; or —$SO_2$—$CF_3$.

2. The compound of the formula I according to claim 1 where n is zero or 1,

U is: —($C_1$-$C_4$)-alkylene-Het-Z, where Het is selected from the group consisting of acridinyl, azepinyl, azetidinyl, benzimidazalinyl, benzimida-zolyl, benzoxazolyl, benzothiazolyl, benzotriazolyl, benzotetrazolyl, benzisoxazolyl, benzisothiazolyl, carbolinyl, quinazolinyl, quinolinyl, 4H-quinolizinyl, quinoxalinyl, quinuclidinyl, cinnolinyl, decahydroquinolinyl, furazanyl, imidazolidinyl, imidazolinyl, imidazolyl, 1H-indazolyl, indolinyl, indolizinyl, indolyl, 3H-indolyl, isoindazolyl, isoindolinyl, isoindolyl, isoquinolinyl, isothiazolidinyl, 2-isothiazolinyl, isothiazolyl, isoxazolyl, isoxazolinyl, 2-isoxazolinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, phenanthridinyl, phenanthrolinyl, phthalazinyl, pteridinyl, purinyl, pyrazolidinyl, pyrazolinyl, pyrazolyl, pyridazinyl, pyridooxazolyl, pyridoimidazolyl, pyridothiazolyl, pyridyl, pyrimidinyl, pyrrolidinyl, pyrrolinyl, 2H-pyrrolyl, pyrrolyl, tetrahydroisoquinolinyl, tetrahydroquinolinyl, tetrahydropyridinyl, 6H-1,2,5-thiadazinyl, 1,2,3-thiadiazolyl, 1,2,4-thiadiazolyl, 1,2,5-thiadiazolyl, 1,3,4-thiadiazolyl, thiazolyl, thienothiazolyl, thienooxazolyl, thienoimidazolyl, thienopyridinyl, triazinyl, 1,2,3-triazolyl, 1,2,3-triazolyl, 1,2,4-triazolyl, 1,2,5-triazolyl and 1,3,4-triazolyl, where Het is unsubstituted or mono- or disubstituted by —($C_1$-$C_3$)-alkyl, —O—($C_1$-$C_3$)-alkyl or —$CF_3$, or —($C_0$-$C_2$)-alkylene-($C_3$-$C_8$)-cycloalkyl-($C_1$-$C_2$)-alkylene-Z, where Z is amino, amidino or guanidino, R is: a hydrogen atom; —($C_3$-$C_6$)-cycloalkyl; —($C_1$-$C_{10}$)-alkylene-O—C(O)—O—R1; or —($C_0$-$C_3$)-alkylene-($C_6$-$C_{14}$)-aryl, where aryl is selected from the group consisting of anthryl, fluorenyl, indanyl, naphthyl, phenyl and tetrahydronaphthalenyl and is unsubstituted or independently mono-, di- or trisubstituted by R1, V is: a hydrogen atom; —($C_1$-$C_4$)-alkyl; halogen, where halogen is selected from the group consisting of fluorine, chlorine, bromine and iodine; —($C_6$-$C_{14}$)-aryl, where aryl is as defined above; —$NO_2$; —$NH_2$; —OH, or —$CF_3$;

W is —($C_1$-$C_4$)-alkylene, where alkylene is unsubstituted or substituted by F or Cl, X is: an aromatic five- to thirteen-membered heterocycle selected from the group consisting of acridinyl, benzimidazalinyl, benzimidazolyl, benzofuranyl, benzothiofuranyl, benzothiophenyl, benzoxazolyl, benzothiazolyl, benzotriazolyl, benzotetrazolyl, benzisoxazolyl, benzisothiazolyl, carbazolyl, beta-carbolinyl, quinazolinyl, quinolizinyl, quinoxalinyl, chromanyl, chromenyl, cinnolinyl, dibenzofuranyl, dibenzothiophenyl, 2,3-dihydrobenzo[1,4]dioxin, furyl, imidazolyl, 1H-indazolyl, indolinyl, indolizinyl, indolyl, 3H-indolyl, isobenzofuranyl, isoquinolinyl, isochromanyl, isoindazolyl, isoindolinyl, isoindolyl, isothiazolidinyl, 2-isothiazolinyl, isothiazolyl, isoxazolyl, isoxazolidinyl, 2-isoxazolinyl, naphthyridinyl, oxadiazolyl, 1,2,3-oxadiazolyl, 1,2,4-oxadiazolyl, 1,2,5-oxadiazolyl, 1,3,4-oxadiazolyl, oxazolyl, pyrimidinyl, phenanthridinyl, phenanthrenyl, phenazinyl, phenothiazinyl, phenoxathiinyl, phenoxazinyl, phthalazinyl, pteridinyl, purinyl, pyrazinyl, pyroazolidinyl, pyrazolinyl pyrazolyl, pyridazinyl, pyridooxazolyl, pyridoimidazolyl, pyridothiazolyl, pyridothiophenyl, pyridyl, pyrimidinyl, pyrrolyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazinyl, thienyl, thienothiazolyl, thienooxazolyl, thienoimidazolyl, thienopyridinyl, triazinyl, 1,2,3-triazolyl, 1,2,3-triazolyl, 1,2,4-triazolyl, 1,2,5-triazolyl, 1,3,4-triazolyl and xanthenyl, where the heterocycle is unsubstituted or mono-, di- or trisubstituted independently by R1, except for the case where X is pyridyl and Y is a hydrogen atom, Y is: a hydrogen atom, ($C_1$-$C_8$)-alkyl, where alkyl is unsubstituted or mono-, di- or trisubstituted independently by R1; —($C_3$-$C_8$)-cycloalkyl, where cycloalkyl is unsubstituted or mono-, di- or trisubstituted independently by R1; —($C_1$-$C_3$)-perfluoralkyl; —($C_6$-$C_{14}$)-aryl, where aryl is as defined above and is unsubstituted or mono-, di- or trisubstituted independently by R1; or —($C_0$-$C_4$)-alkylene-heterocycle, where the heterocycle is as defined above and is unsubstituted or mono-, di- or trisubstituted independently by R1, if n is the integer zero, or Y is —($C_1$-$C_3$)-perfluoroalkyl; —($C_0$-$C_4$)-alkylene-($C_3$-$C_8$)-cycloalkyl, where cycloalkyl is unsubstituted or mono-, di- or trisubstituted independently by R1; —($C_0$-$C_4$)-alkylene-($C_6$-$C_{14}$)-aryl, where aryl is as defined above and is unsubstituted or mono-, di- or trisubstituted independently by R1; or —($C_0$-$C_4$)-alkylene-heterocycle, where the heterocycle is as defined above and is unsubstituted or mono-, di- or trisubstituted independently by R1, if n is the integer 1, R1 is halogen, where halogen is as defined above; —$NO_2$; —CN; —N(R2)-R3, where R2 and R3 are identical or different and independently of one another are a hydrogen atom, —($C_1$-$C_6$)-alkyl, —($C_0$-$C_3$)-alkylene-($C_6$-$C_{14}$)-aryl, where aryl is as defined above, —($C_0$-$C_3$)-alkylene-Het, where Het is as defined above or —($C_0$-$C_3$)-alkylene-($C_3$-$C_6$)-cycloalkyl, —OH, —C(O)—O—R4, where R4 is a hydrogen atom, —($C_1$-$C_6$)-alkyl, —($C_0$-$C_3$)-alkylene-($C_6$-$C_{14}$)-Aryl, where aryl is as defined above, —($C_0$-$C_3$)-alkylene-Het, where Het is as defined above, or —($C_0$-$C_3$)-alkylene-($C_3$-$C_6$)-cycloalkyl; —C(O)—N(R2)-R3, where R2 and R3 are identical or different and independently of one another are as defined above; —O—$CF_3$; —($C_0$-$C_4$)-alkylene-($C_6$-$C_{14}$)-aryl, where aryl is as defined above and is unsubstituted or mono-, di- or trisubstituted independently by halogen or —O—($C_1$-$C_8$)-alkyl, where halogen is as defined above; —($C_0$-$C_4$)-alkylene-($C_3$-$C_6$)-cycloalkyl; —($C_1$-$C_8$)-alkyl, where alkyl is unsubstituted or mono-, di- or trisubstituted independently by halogen, —$NH_2$, —OH or methoxy, where halogen is as defined above; —O—($C_1$-$C_8$)-alkyl, where alkyl is unsubstituted or mono-, di- or trisubstituted independently by halogen, —$NH_2$, —OH or methoxy, where halogen is as defined above; —O—($C_1$-$C_4$)-alkylene-($C_6$-$C_{14}$)-aryl, where aryl is as defined above and is unsubstituted or mono-, di- or trisubstituted independently by halogen or —O—($C_1$-$C_8$)-alkyl, where halogen is as defined above; —$SO_2$—$CH_3$; or —$SO_2$—$CF_3$.

3. The compound of the formula I according to claim 1, where U is the radical

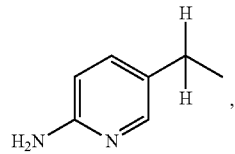

and the pyridyl moiety in the radical is unsubstituted or substituted by methyl or ethyl, n is the integer zero, R is a hydrogen atom or —($C_1$-$C_4$)-alkyl, V is a hydrogen atom, —($C_1$-$C_3$)-alkyl or fluorine, chlorine or bromine, W is —($C_1$-$C_3$)-alkylene, X is an aromatic five- to thirteen-membered heterocycle, where the heterocycle is selected from the group consisting of isoxazolyl, 1,2,3-oxadiazolyl, 1,2,4-oxadiazolyl, 1,2,5-oxadiazolyl, 1,3,4-oxadiazolyl, oxazolyl, 1,2,4-thiadiazolyl, 1,2,5-thiadiazolyl, 1,3,4-thiadiazolyl, thienopyridinyl or thienyl, and the heterocycle is unsubstituted or mono-, di- or trisubstituted independently by R1, Y is —($C_1$-$C_6$)-alkyl, where alkyl is unsubstituted or mono-, di- or trisubstituted independently by R1; —$CF_3$; —($C_3$-$C_6$)-cycloalkyl, where cycloalkyl is unsubstituted or mono-, di- or trisubstituted independently by R1; —($C_6$-$C_{14}$)-aryl, where aryl is selected from the group consisting of indanyl, naphthyl, phenyl or tetrahydronaphthalenyl, where aryl is unsubstituted or mono-, di- or trisubstituted independently by R1; or a heterocycle, where the heterocycle is selected from the group consisting of 2,3-dihydrobenzo[1,4]dioxin, isoxazolyl, 1,2,3-oxadiazolyl, 1,2,4-oxadiazolyl, 1,2,5-oxadiazolyl, 1,3,4-oxadiazolyl, oxazolyl, 1,2,3-thiadiazolyl, 1,2,4-thiadiazolyl, 1,2,5-thiadiazolyl, 1,3,4-thiadiazolyl, thienopyridinyl, and thienyl, and said heterocycle is unsubstituted or mono-, di- or trisubstituted independently by R1, and R1 is selected from fluorine, chlorine, bromine, —($C_1$-$C_4$)-alkyl, —($C_0$-$C_4$)-alkylene-phenyl, —O—$CH_3$, and —O—($C_1$-$C_4$)-alkylene-phenyl, where phenyl is unsubstituted or mono- or disubstituted by fluorine, chlorine, bromine or —O—($C_1$-$C_4$)-alkyl, —($C_3$-$C_6$)-cycloalkyl, or —$CF_3$.

4. The compound of formula I of claim 1, selected from:

3-(6-aminopyridin-3-yl)-2-{1-[5-(5-chlorothiophen-2-yl)isoxazol-3-ylmethyl]-1H-imidazol-4-yl}propionic acid, 3-(6-aminopyridin-3-yl)-2-[1-(5-phenylisoxazol-3-ylmethyl)-1H-imidazol-4-yl]propionic acid, 3-(6-aminopyridin-3-yl)-2-{1-[2-(5-chlorothiophen-2-yl)thiazol-5-ylmethyl]-1H-imidazol-4-yl}propionic acid, 3-(6-aminopyridin-3-yl)-2-[1-(6-chlorothieno[2,3-b]pyridin-2-ylmethyl)-1H-imidazol-4-yl]propionic acid, 3-(6-aminopyridin-3-yl)-2-{1-[5-(4-methoxyphenyl)isoxazol-3-ylmethyl]-1H-imidazol-4-yl}propionic acid, 3-(6-aminopyridin-3-yl)-2-{1-[5-(3-methylbutyl)isoxazol-3-ylmethyl]-1H-imidazol-4-yl}propionic acid, 3-(6-aminopyridin-3-yl)-2-{1-[5-(5-chlorothiophen-2-yl)-[1,3,4]thiadiazol-2-ylmethyl]-1H-imidazol-4-yl}propionic acid, 3-(6-aminopyridin-3-yl)-2-{1-[5-(4-chlorophenyl)-[1,3,4]thiadiazol-2-ylmethyl]-1H-imidazol-4-yl}propionic acid, 3-(6-aminopyridin-3-yl)-2-[1-(5-tert-butyl-[1,3,4]thiadiazol-2-ylmethyl)-1H-imidazol-4-yl]propionic acid, 3-(6-aminopyridin-3-yl)-2-{1-[5-(4-trifluoromethylphenyl)-[1,2,4]oxadiazol-3-ylmethyl]-1H-imidazol-4-yl}propionic acid, 3-(6-aminopyridin-3-yl)-2-{1-[5-(3-trifluoromethylphenyl)-[1,2,4]oxadiazol-3-ylmethyl]-1H-imidazol-4-yl}propionic acid, 3-(6-aminopyridin-3-yl)-2-[1-(5-cyclopropyl-[1,3,4]thiadiazol-2-ylmethyl)-1H-imidazol-4-yl]propionic acid, 3-(6-aminopyridin-3-yl)-2-[1-(5-phenyl-[1,2,4]oxadiazol-3-ylmethyl)-1H-imidazol-4-yl]propionic acid, 3-(6-aminopyridin-3-yl)-2-{1-[3-(3,4-dimethoxyphenyl)-[1,2,4]oxadiazol-5-ylmethyl]-1H-imidazol-4-yl}propionic acid, 3-(6-aminopyridin-3-yl)-2-{1-[3-(4-methoxyphenyl)-[1,2,4]oxadiazol-5-ylmethyl]-1H-imidazol-4-yl}propionic acid, 3-(6-aminopyridin-3-yl)-2-{1-[3-(4'-isopropylphenyl)-[1,2,4]oxadiazol-5-ylmethyl]-1H-imidazol-4-yl}propionic acid, 3-(6-aminopyridin-3-yl)-2-{1-[3-(4"-tert-butylphenyl)-[1,2,4]oxadiazol-5-ylmethyl]-1H-imidazol-4-yl}propionic acid, 3-(6-aminopyridin-3-yl)-2-{1-[5-(2-methylthiazol-4-yl)isoxazol-3-ylmethyl]-1H-imidazol-4-yl}propionic acid, 3-(6-aminopyridin-3-yl)-2-{1-[5-(3,4-dichlorophenyl)isoxazol-3-ylmethyl]-1H-imidazol-4-yl}propionic acid, 3-(6-aminopyridin-3-yl)-2-{1-[3-(4-methoxyphenyl)-[1,2,4]oxadiazol-5-ylmethyl]-1H-imidazol-4-yl}propionic acid, 3-(6-aminopyridin-3-yl)-2-[1-(5-phenyl-[1,3,4]thiadiazol-2-ylmethyl)-1H-imidazol-4-yl]propionic acid, 3-(6-aminopyridin-3-yl)-2-{1-[5-(4-methoxyphenyl)-[1,3,4]thiadiazol-2-ylmethyl]-1H-imidazol-4-yl}propionic acid, 3-(6-aminopyridin-3-yl)-2-{1-[5-(3,5-dimethylisoxazol-4-yl)-[1,2,4]oxadiazol-3-ylmethyl]-1H-imidazol-4-yl}propionic acid, 3-(6-aminopyridin-3-yl)-2-{1-[5-thiophen-2-ylisoxazol-3-ylmethyl]-1H-imidazol-4-yl}propionic acid, 3-(6-aminopyridin-3-yl)-2-[1-(5-tert-butyl-1,2,4-oxadiazol-3-ylmethyl)-1H-imidazol-4-yl]propionic acid, 3-(6-aminopyridin-3-yl)-2-(1-{3-[4-(4-chlorobenzyloxy)phenyl]-[1,2,4]oxadiazol-5-ylmethyl}-1H-imidazol-4-yl)propionic acid, 3-(6-aminopyridin-3-yl)-2-[1-(4-bromothiophen-2-ylmethyl)-1H-imidazol-4-yl]propionic acid, 3-(6-aminopyridin-3-yl)-2-[1-(5-methylisoxazol-3-ylmethyl)-1H-imidazol-4-yl]propionic acid, 3-(6-aminopyridin-3-yl)-2-[1-(4-phenyl-5-trifluoromethylthiophen-2-ylmethyl)-1H-imidazol-4-yl]propionic acid, 3-(6-aminopyridin-3-yl)-2-{1-[5-(4-bromophenyl)isoxazol-3-ylmethyl]-1H-imidazol-4-yl}propionic acid, 3-(6-aminopyridin-3-yl)-2-[1-(5-p-tolylisoxazol-3-ylmethyl)-1H-imidazol-4-yl]propionic acid, 3-(6-aminopyridin-3-yl)-2-(1-{2-[5-(5-chlorothiophen-2-yl)isoxazol-3-yl]-ethyl}-1H-imidazol-4-yl)propionic acid, 3-(6-aminopyridin-3-yl)-2-{1-[5-(4-isobutylphenyl)isoxazol-3-ylmethyl]-1H-imidazol-4-yl}propionic acid, 3-(6-aminopyridin-3-yl)-2-[1-(5-cyclopentyl-[1,3,4]thiadiazol-2-ylmethyl)-1H-imidazol-4-yl]propionic acid, 3-(6-aminopyridin-3-yl)-2-[1-(5-cyclobutyl-[1,3,4]thiadiazol-2-ylmethyl)-1H-imidazol-4-yl]propionic acid, 3-(6-aminopyridin-3-yl)-2-[1-(5-cyclopropylisoxazol-3-ylmethyl)-1H-imidazol-4-yl]propionic acid, 3-(6-aminopyridin-3-yl)-2-[1-(5-cyclohexylisoxazol-3-ylmethyl)-1H-imidazol-4-yl]propionic acid, 3-(6-aminopyridin-3-yl)-2-[1-(5-cyclohexyl-[1,3,4]thiadiazol-2-ylmethyl)-1H-imidazol-4-yl]propionic acid, 3-(6-aminopyridin-3-yl)-2-{1-[5-(3-methylbutyl)-[1,3,4]thiadiazol-2-ylmethyl]-1H-imidazol-4-yl}propionic acid, 3-(6-aminopyridin-3-yl)-2-[1-(5-cyclobutylisoxazol-3-yl-methyl)-1H-imidazol-4-yl]propionic acid, 3-(6-aminopyridin-3-yl)-2-{1-[5-(4-fluorophenyl)isoxazol-3-ylmethyl]-1H-imidazol-4-yl}propionic acid, 3-(6-aminopyridin-3-yl)-2-{1-[5-(4-benzylphenyl)isoxazol-3-ylmethyl]-1H-imidazol-4-yl}propionic acid, 3-(6-aminopyridin-3-yl)-2-{1-[5-(4-tert-butylphenyl)isoxazol-3-ylmethyl]-1H-imidazol-4-yl}propionic acid, 3-(6-aminopyridin-3-yl)-2-{1-[5-(4-tert-butyl-2,6-dimethylphenyl)isoxazol-3-ylmethyl]-1H-imidazol-4-yl}propionic acid, 3-(6-aminopyridin-3-yl)-2-{1-[5-(2-chlorophenyl)isoxazol-3-ylmethyl]-1H-imidazol-4-yl}propionic acid, 3-(6-aminopyridin-3-yl)-2-{1-[5-(4-sec-butylphenyl)isoxazol-3-ylmethyl]-1H-imidazol-4-yl}propionic acid, 3-(6-aminopyridin-3-yl)-2-[1-(5-indan-5-ylisoxazol-3-yl-methyl)-1H-imidazol-4-yl]propionic acid, 3-(6-aminopyridin-3-yl)-2-{1-[5-(4-cyclopentylphenyl)isoxazol-3-ylmethyl]-1H-imidazol-4-yl}propionic acid, 3-(6-aminopyridin-3-yl)-2-{1-[5-(4-isopropylphenyl)isoxazol-3-ylmethyl]-1H-imidazol-4-yl}propionic acid, 3-(6-aminopyridin-3-yl)-2-{1-[5-(4-butylphenyl)isoxazol-3-ylmethyl]-1H-imidazol-4-yl}propionic acid, 3-(6-aminopyridin-3-yl)-2-{1-[5-(4-cyclohexylphenyl)isoxazol-3-ylmethyl]-1H-imidazol-4-yl}propionic acid, 3-(6-aminopyridin-3-yl)-2-{1-[5-(5,6,7,8-tetrahydronaphthalen-2-yl)isoxazol-3-ylmethyl]-1H-imidazol-4-yl}propionic acid, 3-(6-aminopyridin-3-yl)-2-{1-[5-(4-propylphenyl)isoxazol-3-ylmethyl]-1H-imidazol-4-yl}propionic acid, 3-(6-aminopyridin-3-yl)-2-{1-[5-(4-phenethylphenyl)isoxazol-3-ylmethyl]-1H-imidazol-4-yl}propionic acid, 3-(6-aminopyridin-3-yl)-2-{1-[5-(2,3-dihydrobenzo[1,4]dioxin-6-yl)isoxazol-3-ylmethyl]-1H-imidazol-4-yl}propionic acid, ethyl (S)-3-(6-aminopyridin-3-yl)-2-{1-[5-(5-chlorothiophen-2-yl)isoxazol-3-ylmethyl]-1H-imidazol-4-yl}propionate, ethyl (R)-3-(6-aminopyridin-3-yl)-2-{1-[5-(5-chlorothiophen-2-yl)isoxazol-3-ylmethyl]-1H-imidazol-4-yl}propionate, (S)-3-(6-aminopyridin-3-yl)-2-{1-[5-(5-chlorothiophen-2-yl)isoxazol-3-ylmethyl]-1H-imidazol-4-yl}propionic acid, (R)-3-(6-aminopyridin-3-yl)-2-{1-[5-(5-chlorothiophen-2-yl)isoxazol-3-ylmethyl]-1H-imidazol-4-yl}propionic acid, or 3-(6-amino-5-methylpyridin-3-yl)-2-[1-(5-cyclopropyl-[1,3,4]thiadiazol-2-ylmethyl)-1H-imidazol-4-yl]propionic acid.

5. A medicament having an effective content of at least one compound of the formula I of claim 1 together with a pharmaceutically suitable and physiologically tolerated carrier, additive and/or other active ingredients and excipients.

6. The compound as claimed in claim 1, wherein Y is selected from: —($C_0$-$C_4$)-alkylene-($C_3$-$C_{12}$)-cycloalkyl, wherein cycloalkyl is unsubstituted or mono-, di- or trisubstituted independently by R1; —($C_0$-$C_4$)-alkylene-($C_6$-$C_{14}$)-aryl, wherein aryl is unsubstituted or mono-, di- or trisubstituted independently by R1; and —($C_0$-$C_4$)-alkylene-heterocycle, wherein heterocycle is an aromatic five- to thirteen-membered heterocycle whose ring systems contain 5 to 13 carbon atoms, which are present in one, two or three ring systems attached to one another, and which may contain one, two, three or four identical or different heteroatoms from the group consisting of oxygen, nitrogen, and sulfur, wherein the heterocycle is unsubstituted or mono-, di- or trisubstituted independently by R1.

\* \* \* \* \*